United States Patent [19]
Blewett et al.

[11] Patent Number: 5,995,875
[45] Date of Patent: Nov. 30, 1999

[54] APPARATUS FOR THERMAL TREATMENT OF TISSUE

[75] Inventors: Jeffrey J. Blewett, Plantsville; Christopher W. Maurer; Corbett W. Stone, both of Newtown, all of Conn.

[73] Assignee: United States Surgical, Norwalk, Conn.

[21] Appl. No.: 08/942,351

[22] Filed: Oct. 1, 1997

[51] Int. Cl.⁶ .................................................. A61B 17/39
[52] U.S. Cl. ................................ 607/98; 607/101; 606/41
[58] Field of Search ........................ 607/98–102; 606/41, 606/46, 49, 50, 37

[56] References Cited

U.S. PATENT DOCUMENTS

| | | |
|---|---|---|
| Re. 32,057 | 12/1985 | LeVeen . |
| Re. 32,066 | 1/1986 | Leveen . |
| 3,991,770 | 11/1976 | LeVeen . |
| 4,011,872 | 3/1977 | Komiya . |
| 4,121,592 | 10/1978 | Whalley . |
| 4,154,246 | 5/1979 | LeVeen . |
| 4,237,898 | 12/1980 | Whalley . |
| 4,280,503 | 7/1981 | Ackerman . |
| 4,311,154 | 1/1982 | Sterzer et al. . |
| 4,411,266 | 10/1983 | Cosman . |
| 4,423,727 | 1/1984 | Widran et al. . |
| 4,448,198 | 5/1984 | Turner . |
| 4,503,855 | 3/1985 | Maslanka . |
| 4,565,200 | 1/1986 | Cosman . |
| 4,601,296 | 7/1986 | Yerushalmi . |
| 4,658,836 | 4/1987 | Turner . |
| 4,676,258 | 6/1987 | Inokuchi et al. . |

(List continued on next page.)

FOREIGN PATENT DOCUMENTS

| | | |
|---|---|---|
| 0608609 | 8/1994 | European Pat. Off. . |
| 2941060 | 4/1980 | Germany . |
| 3247793 | 7/1983 | Germany . |
| 9419137 | 1/1995 | Germany . |

(List continued on next page.)

OTHER PUBLICATIONS

RADIONICS® Neurosurgical Instruments, 1981 Radionics, Inc.

Olinger et al., "Eighteen–Gauge Microscopic–Telescopic Needle Endoscope with Electrode Channel: Potential Clinical and Research Application", *Surgical Neurology*, May 1974, pp. 151–159.

*Primary Examiner*—Linda C. M. Dvorak
*Assistant Examiner*—Roy Gibson

[57] ABSTRACT

An auxiliary electromagnetic thermal treatment apparatus for use with an endoscope to provide the endoscope with electromagnetic thermal treatment capabilities includes a handle portion and an elongate portion connected to the handle portion and dimensioned to be at least partially inserted within a working channel of an endoscope. The elongate portion includes at least one delivery tube having a memory portion comprised of a shape memory material and defining a normally unstressed curved configuration. The delivery tube is longitudinally moveable relative to the handle portion to extend the memory portion beyond the working channel of the endoscope such that the memory portion assumes the normal unstressed curved configuration thereof. An electromagnetic probe is disposed within the delivery tube and is longitudinally moveable relative to the delivery tube to extend a probe end portion thereof beyond the delivery tube and within tissue. The electromagnetic probe is adapted to follow the curved configuration of the memory portion of the delivery tube for deployment at an angularly oriented relation with respect to the endoscope. A rotatable control member is mounted to the handle portion and operatively connected to the one delivery tube. The control member is rotatable to move the delivery tube between a first retracted position and a second advanced position. An actuator is also mounted to the handle portion and is operatively connected to the electromagnetic probe. The actuator is moveable to extend the probe end portion beyond the delivery tube. A combination of an endoscope and an auxiliary thermal treatment device and a method for thermally treating tissue is also provided.

25 Claims, 28 Drawing Sheets

U.S. PATENT DOCUMENTS

| | | |
|---|---|---|
| 4,763,671 | 8/1988 | Goffinet . |
| 4,805,616 | 2/1989 | Pao . |
| 4,823,791 | 4/1989 | D'Amelio et al. . |
| 4,896,671 | 1/1990 | Cunningham et al. . |
| 4,907,589 | 3/1990 | Cosman . |
| 4,917,082 | 4/1990 | Grossi et al. . |
| 4,920,978 | 5/1990 | Colvin . |
| 4,950,267 | 8/1990 | Ishihara et al. . |
| 4,955,377 | 9/1990 | Lennox et al. . |
| 4,966,597 | 10/1990 | Cosman . |
| 4,979,948 | 12/1990 | Geddes et al. . |
| 5,007,908 | 4/1991 | Rydell . |
| 5,057,107 | 10/1991 | Parins et al. . |
| 5,078,716 | 1/1992 | Doll . |
| 5,083,565 | 1/1992 | Parins . |
| 5,084,044 | 1/1992 | Quint . |
| 5,098,431 | 3/1992 | Rydell . |
| 5,151,100 | 9/1992 | Abele et al. . |
| 5,159,925 | 11/1992 | Neuwirth et al. . |
| 5,186,181 | 2/1993 | Fanconi et al. . |
| 5,191,883 | 3/1993 | Lennox et al. . |
| 5,192,280 | 3/1993 | Parins . |
| 5,197,963 | 3/1993 | Parins . |
| 5,220,927 | 6/1993 | Astrahan et al. . |
| 5,246,438 | 9/1993 | Langberg . |
| 5,249,585 | 10/1993 | Turner et al. . |
| 5,273,524 | 12/1993 | Fox et al. . |
| 5,282,799 | 2/1994 | Rydell . |
| 5,290,286 | 3/1994 | Parins . |
| 5,295,955 | 3/1994 | Rosen et al. . |
| 5,300,068 | 4/1994 | Rosar et al. . |
| 5,301,687 | 4/1994 | Wong et al. . |
| 5,304,214 | 4/1994 | DeFord et al. . |
| 5,318,563 | 6/1994 | Malis et al. . |
| 5,330,518 | 7/1994 | Neilson et al. . |
| 5,334,193 | 8/1994 | Nardella . |
| 5,341,807 | 8/1994 | Nardella . |
| 5,342,357 | 8/1994 | Nardella . |
| 5,364,392 | 11/1994 | Warner et al. . |
| 5,368,591 | 11/1994 | Lennox et al. . |
| 5,370,675 | 12/1994 | Edwards et al. . |
| 5,383,876 | 1/1995 | Nardella . |
| 5,383,917 | 1/1995 | Desai et al. . |
| 5,385,544 | 1/1995 | Edwards et al. . |
| 5,401,274 | 3/1995 | Kusunoki . |
| 5,403,311 | 4/1995 | Abele et al. . |
| 5,409,006 | 4/1995 | Buchholtz et al. . |
| 5,409,453 | 4/1995 | Lundquist et al. . |
| 5,413,588 | 5/1995 | Rudie et al. . |
| 5,421,819 | 6/1995 | Edwards et al. . |
| 5,423,808 | 6/1995 | Edwards et al. . |
| 5,431,649 | 7/1995 | Mulier et al. . |
| 5,435,805 | 7/1995 | Edwards et al. . |
| 5,437,662 | 8/1995 | Nardella . |
| 5,441,498 | 8/1995 | Perkins . |
| 5,454,782 | 10/1995 | Perkins . |
| 5,458,597 | 10/1995 | Edwards et al. . |
| 5,464,437 | 11/1995 | Reid et al. . |
| 5,464,445 | 11/1995 | Rudie et al. . |
| 5,470,308 | 11/1995 | Edwards et al. . |
| 5,470,309 | 11/1995 | Edwards et al. . |
| 5,472,441 | 12/1995 | Edwards et al. . |
| 5,484,400 | 1/1996 | Edwards et al. . |
| 5,486,161 | 1/1996 | Lax et al. . |
| 5,507,743 | 4/1996 | Edwards et al. . |
| 5,509,929 | 4/1996 | Hascoet et al. . |
| 5,514,130 | 5/1996 | Baker . |
| 5,531,676 | 7/1996 | Edwards et al. . |
| 5,531,677 | 7/1996 | Lundquist et al. . |
| 5,536,240 | 7/1996 | Edwards et al. . |
| 5,540,655 | 7/1996 | Edwards et al. . |
| 5,540,681 | 7/1996 | Strul et al. . |
| 5,542,915 | 8/1996 | Edwards et al. . |
| 5,542,916 | 8/1996 | Hirsch et al. . |
| 5,545,161 | 8/1996 | Imran . |
| 5,599,294 | 2/1997 | Edwards et al. . |
| 5,599,345 | 2/1997 | Edwards et al. . |
| 5,599,346 | 2/1997 | Edwards et al. . |
| 5,609,573 | 3/1997 | Sandock ................................. 604/22 |
| 5,685,878 | 11/1997 | Falwell et al. ........................ 606/49 |

FOREIGN PATENT DOCUMENTS

| | | |
|---|---|---|
| 2121675 | 5/1990 | Japan . |
| 2119253 | 11/1983 | United Kingdom . |
| 9004365 | 5/1990 | WIPO . |
| 9103996 | 4/1991 | WIPO . |
| 9116859 | 11/1991 | WIPO . |
| 9210142 | 6/1992 | WIPO . |
| 9220290 | 11/1992 | WIPO . |
| 9304727 | 3/1993 | WIPO . |
| 9315664 | 8/1993 | WIPO . |
| 9513027 | 5/1995 | WIPO . |
| WO 96 10367 | 4/1996 | WIPO . |
| WO 96 34571 | 11/1996 | WIPO . |
| 9706857 | 2/1997 | WIPO . |

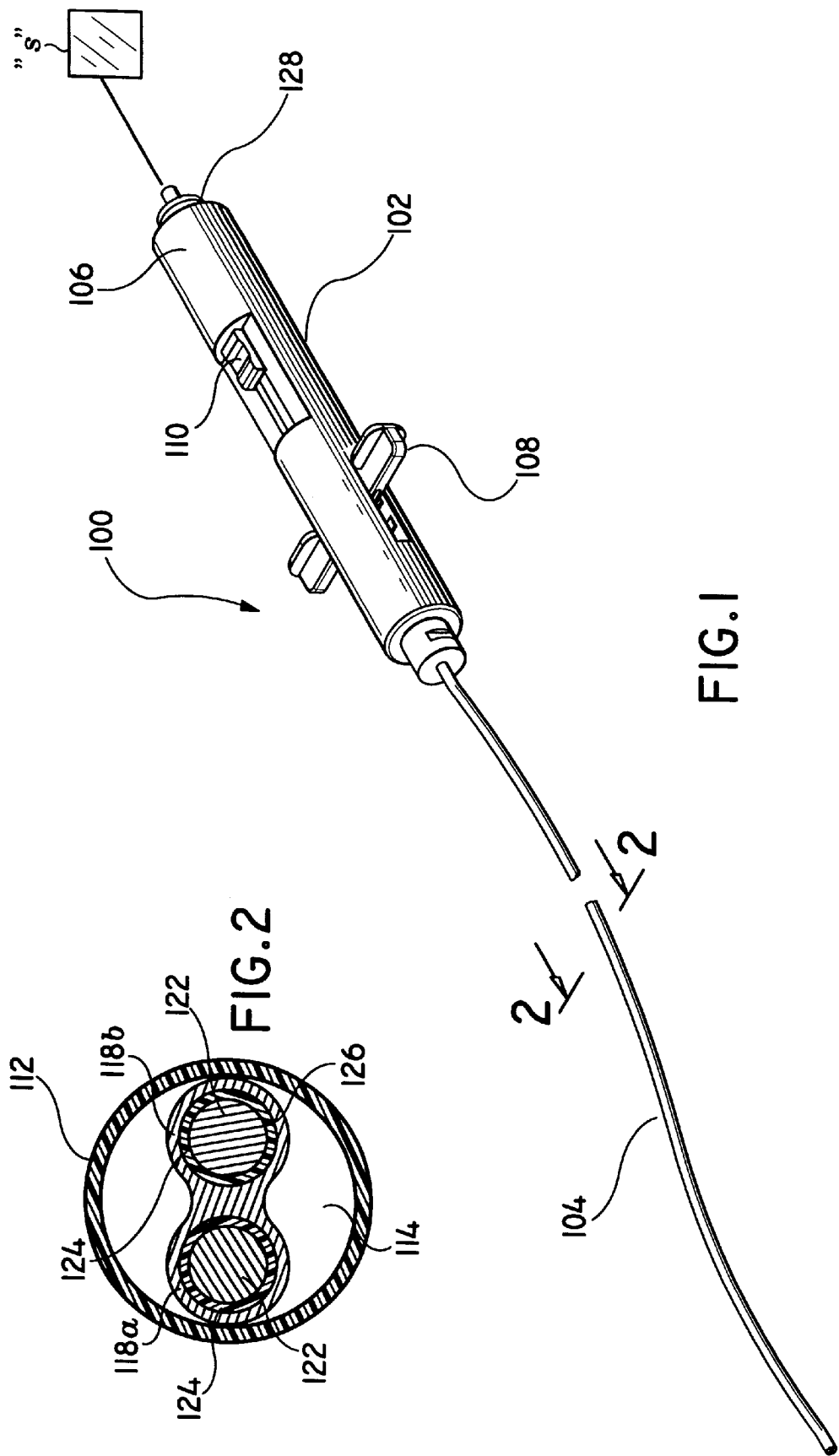

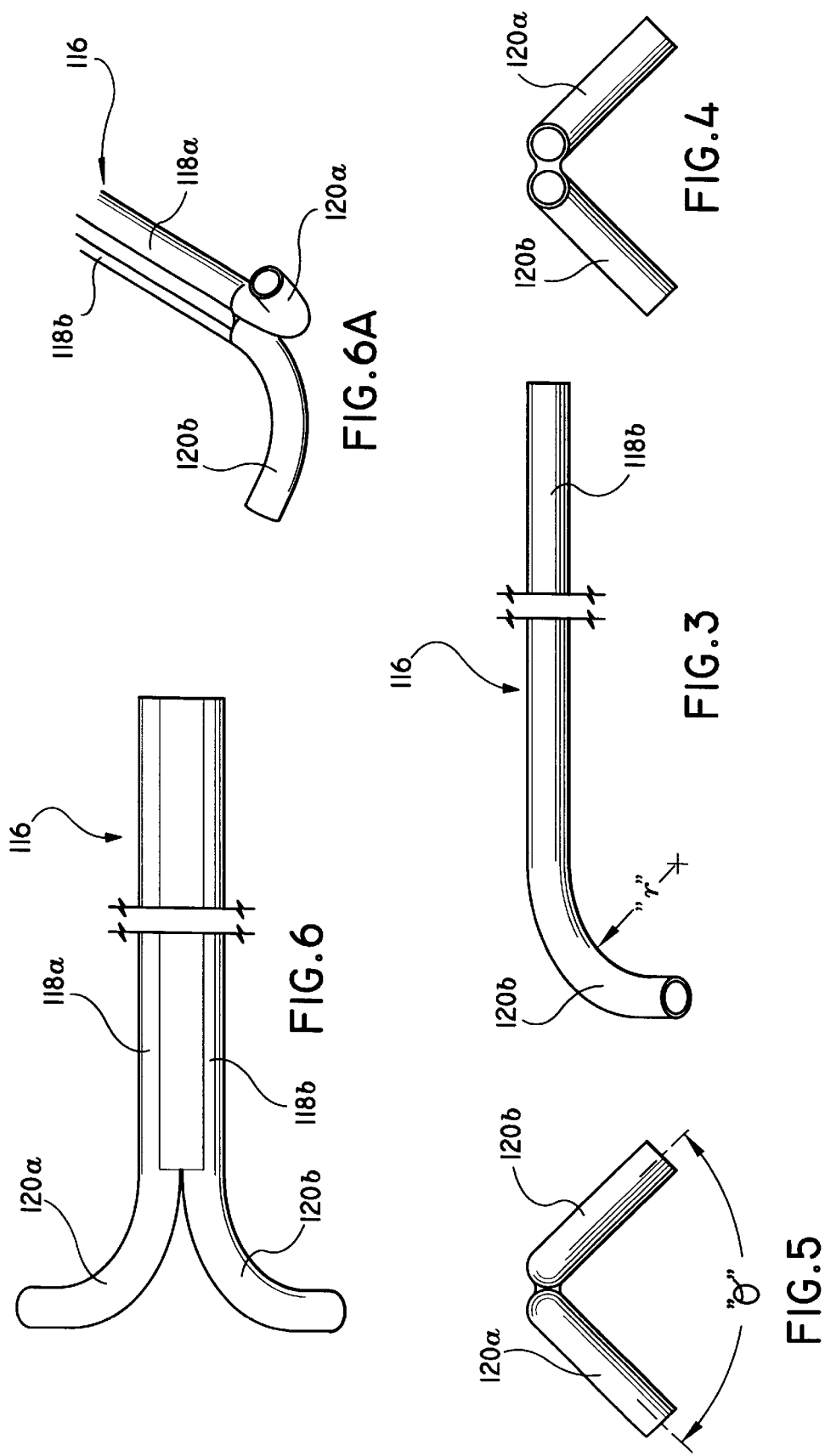

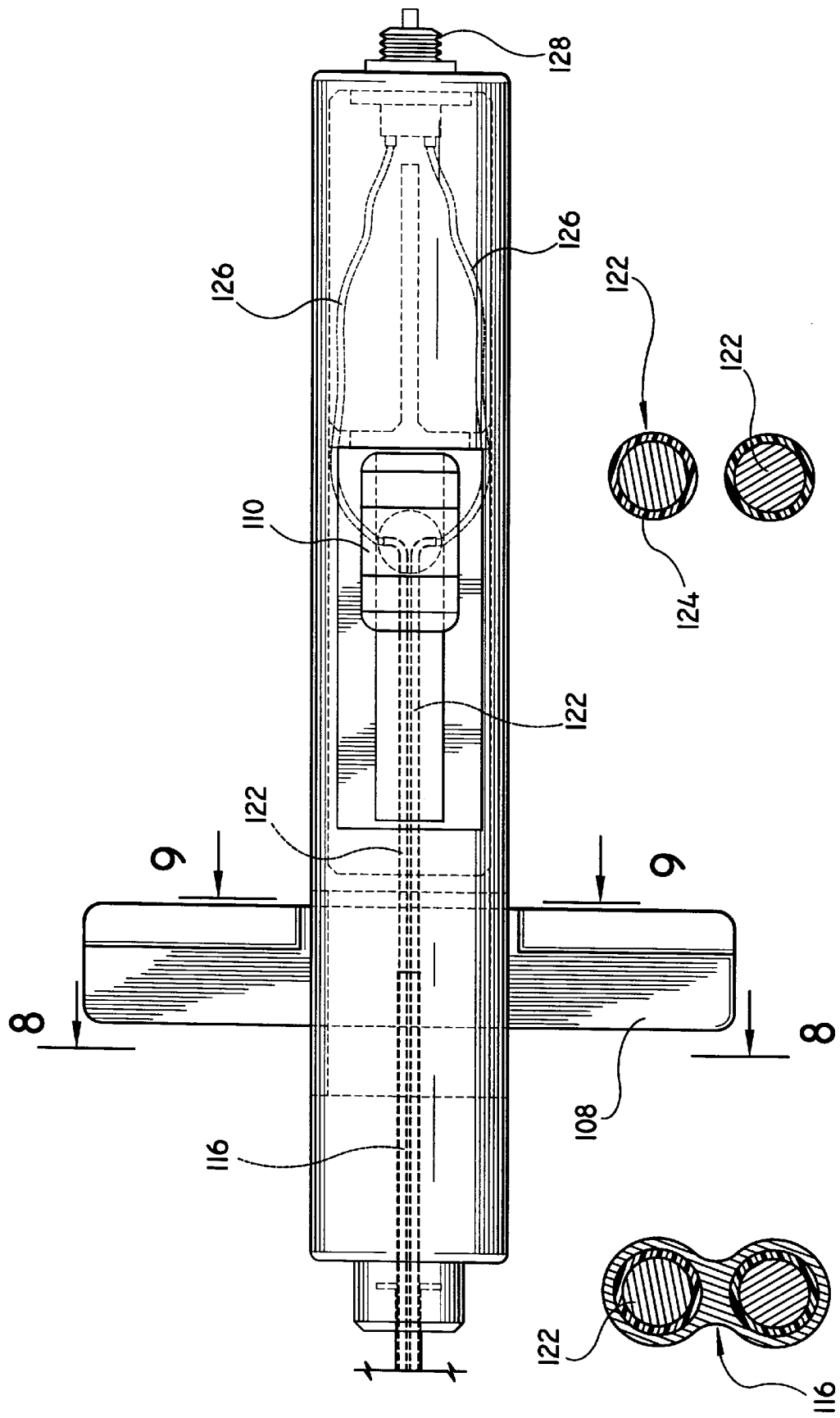

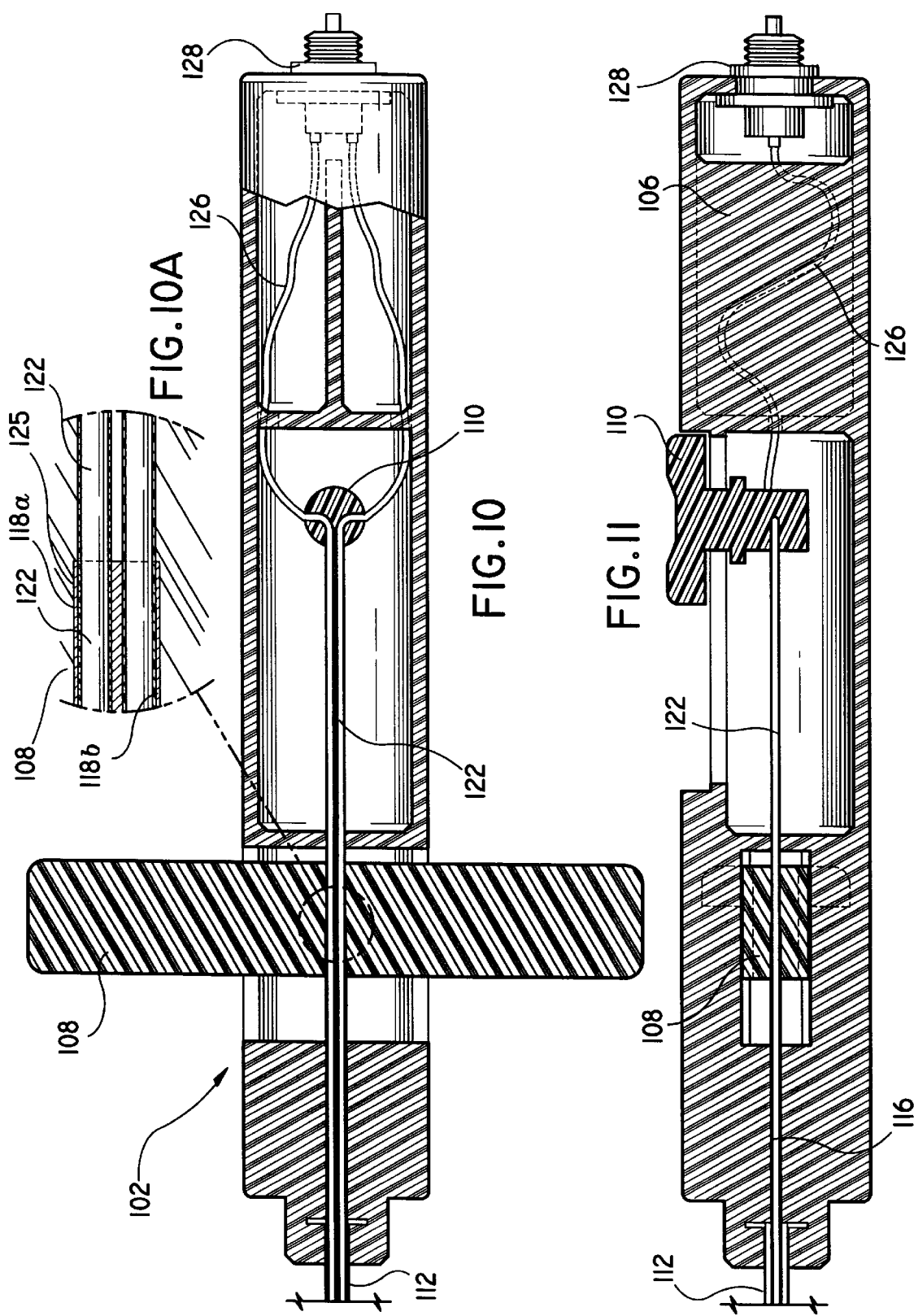

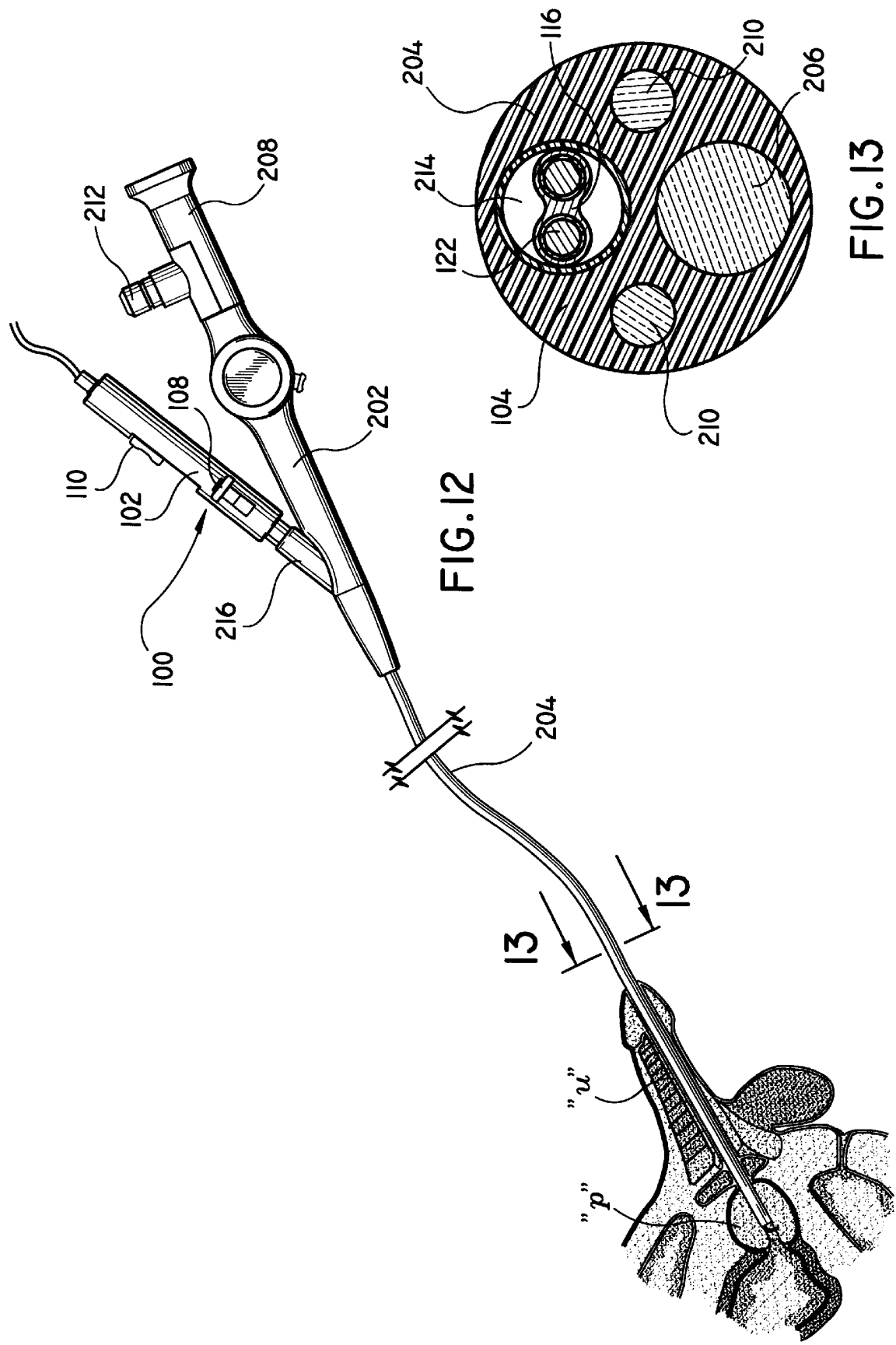

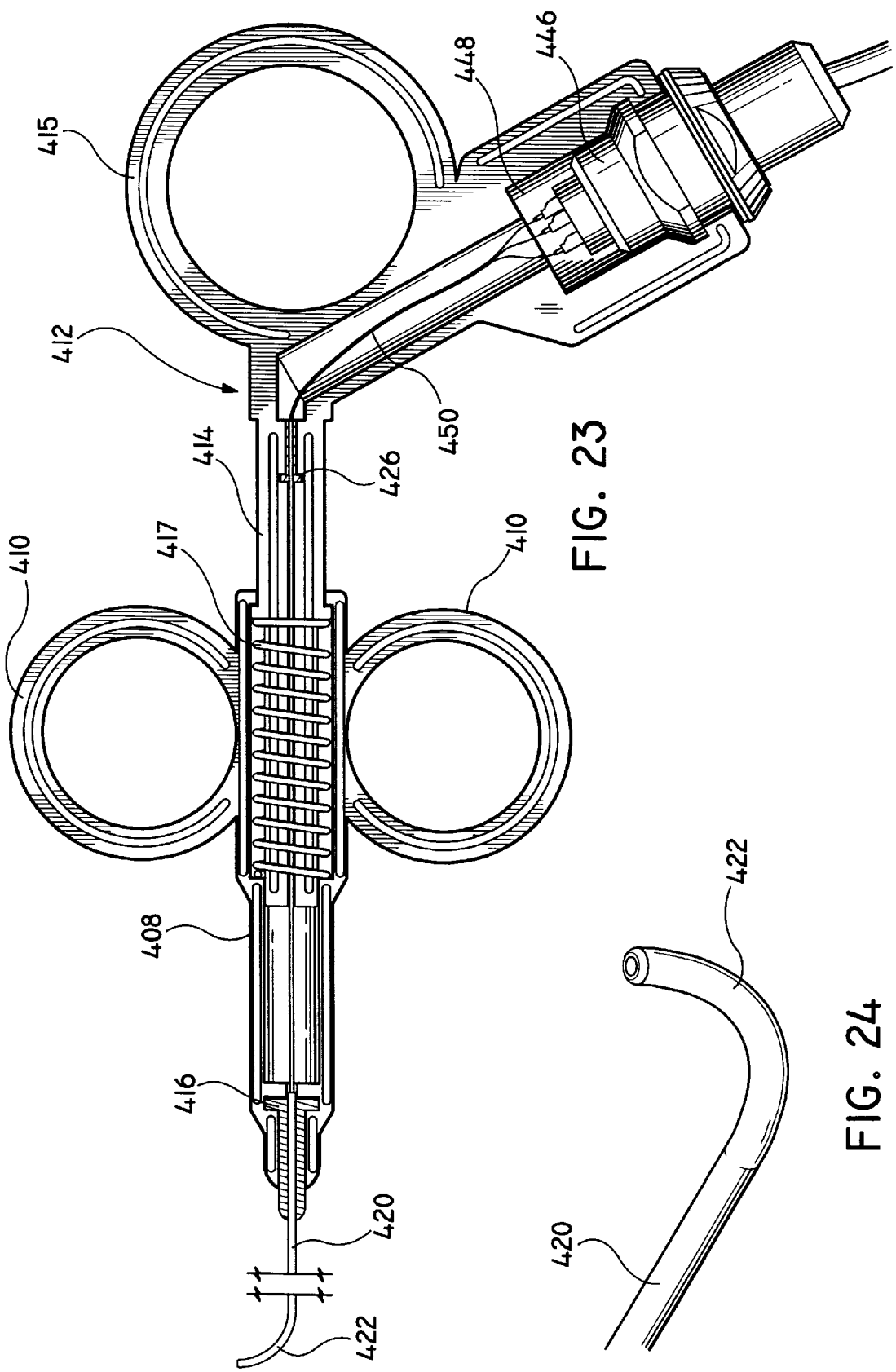

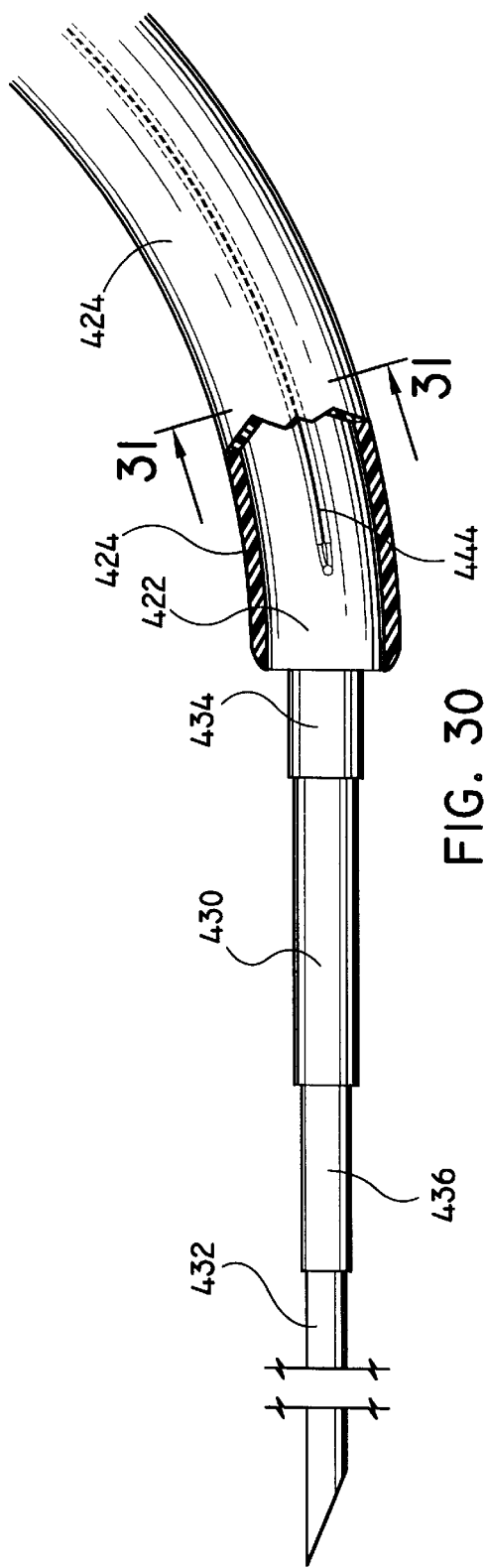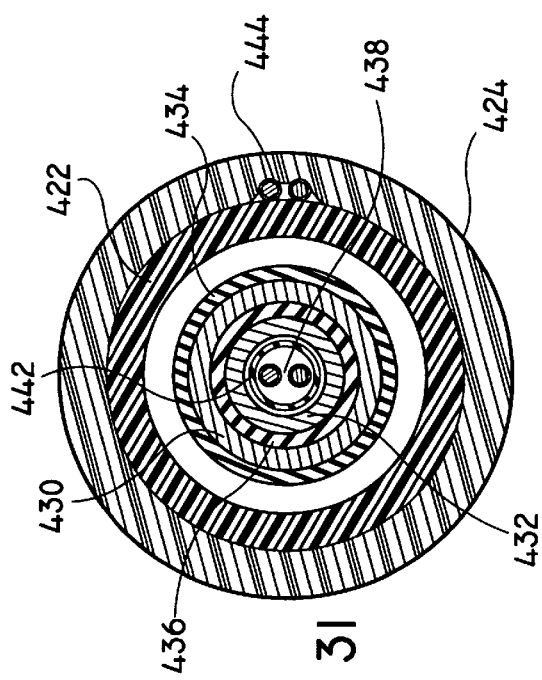
FIG. 30
FIG. 31

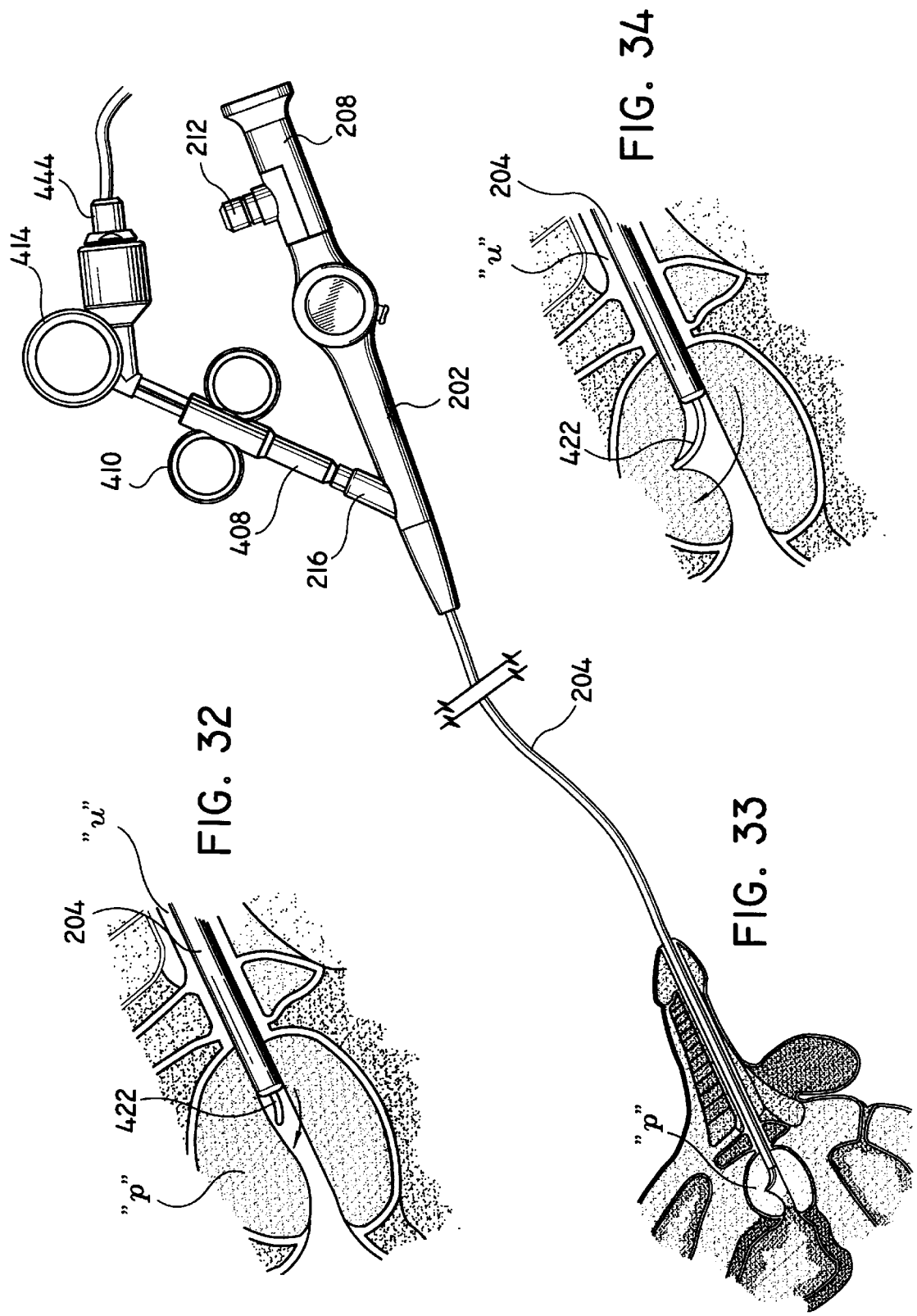

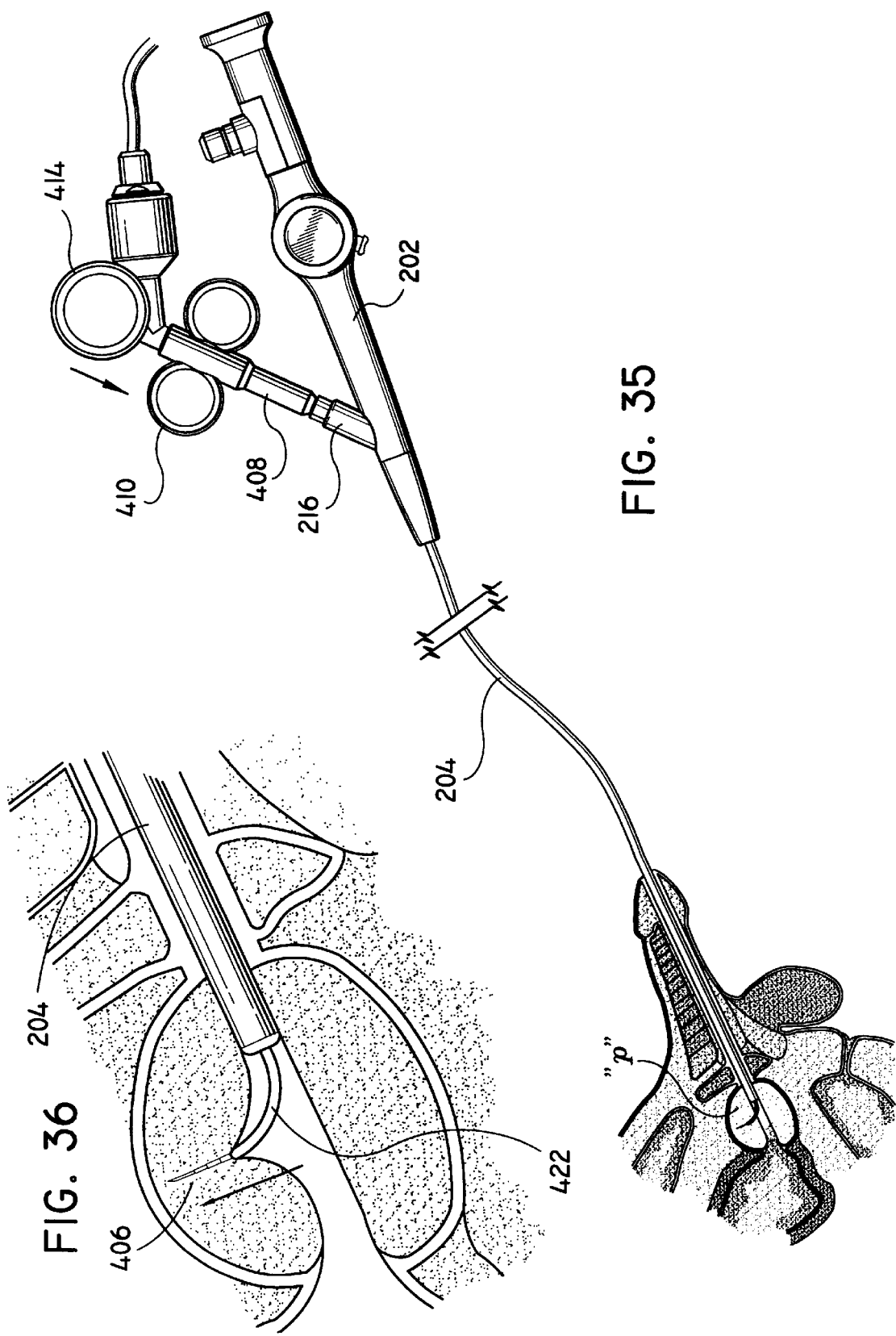

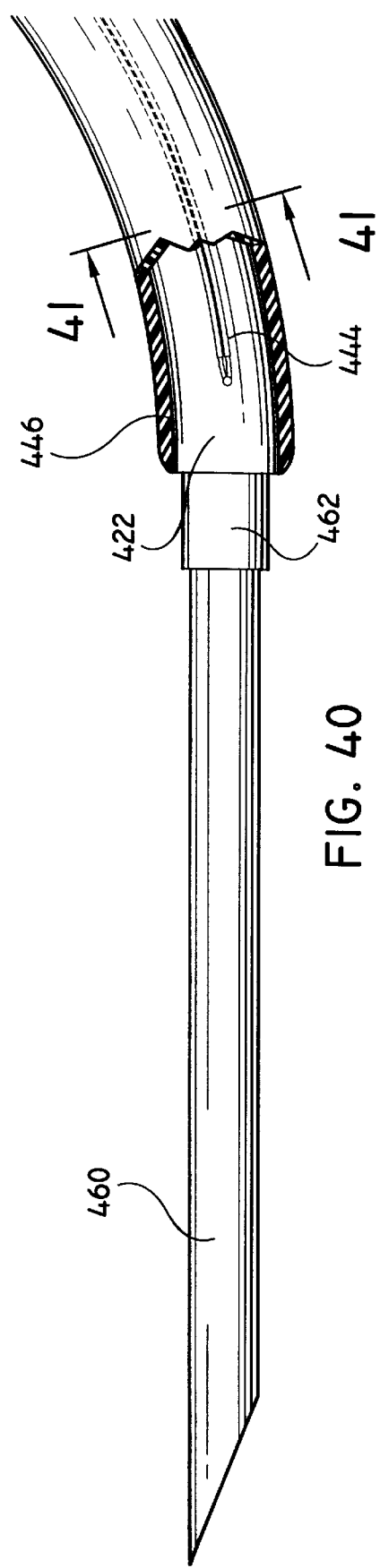
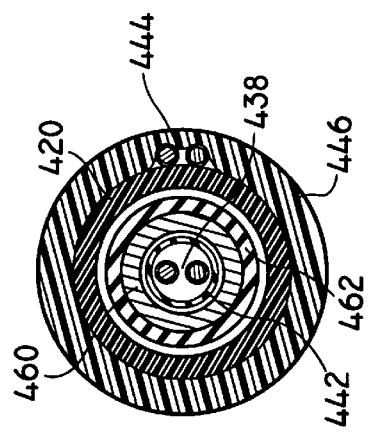
FIG. 40
FIG. 41

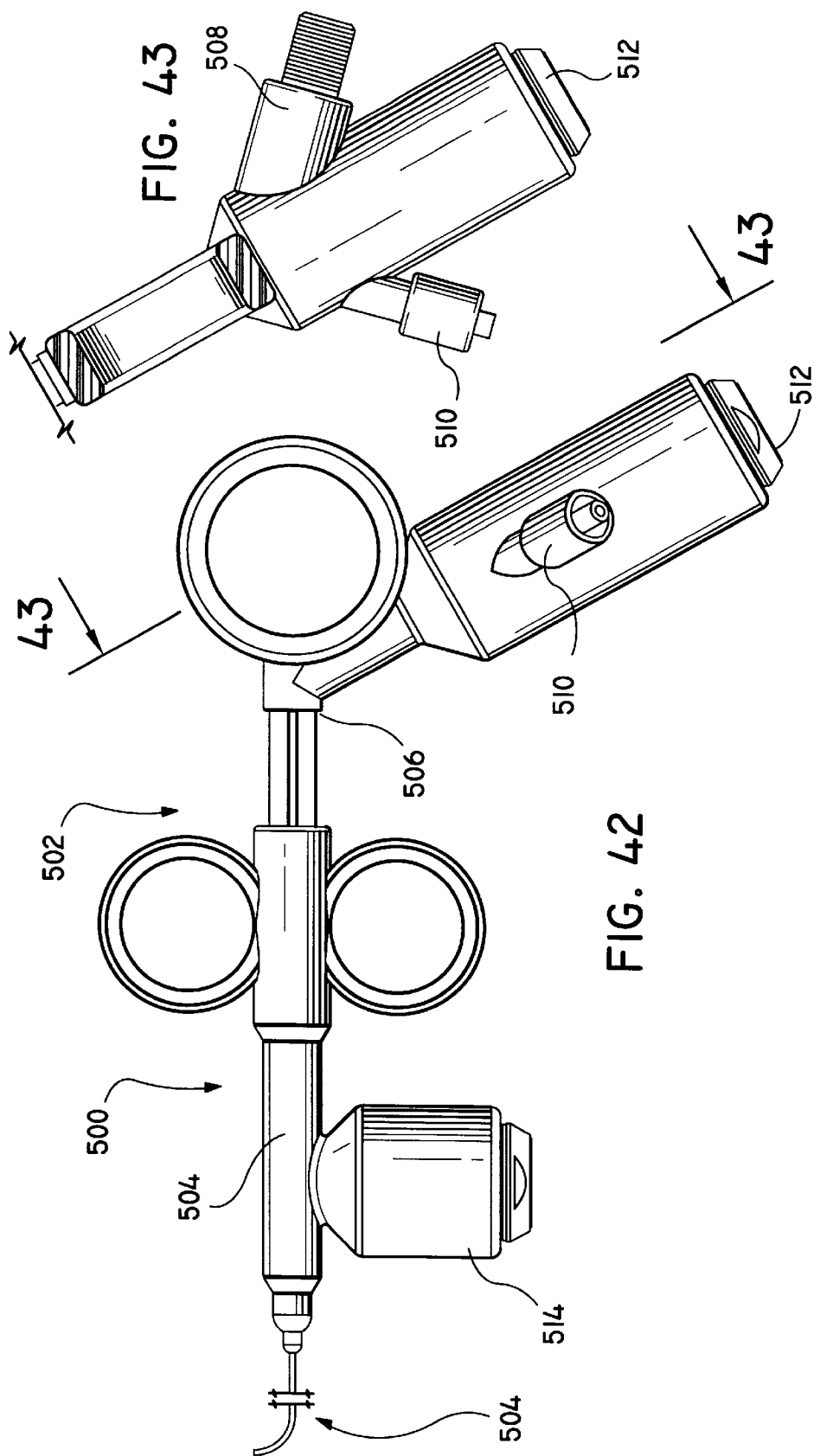

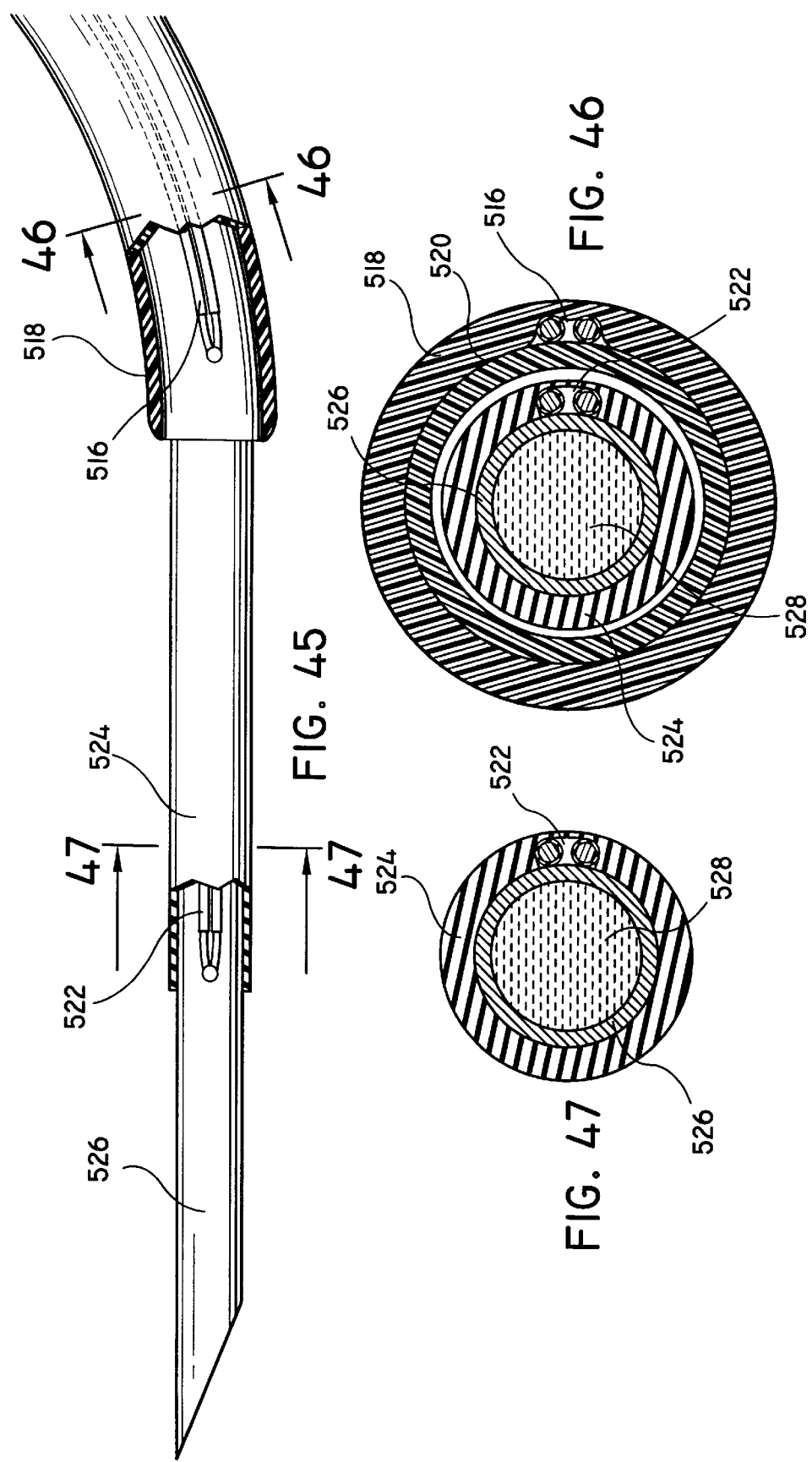

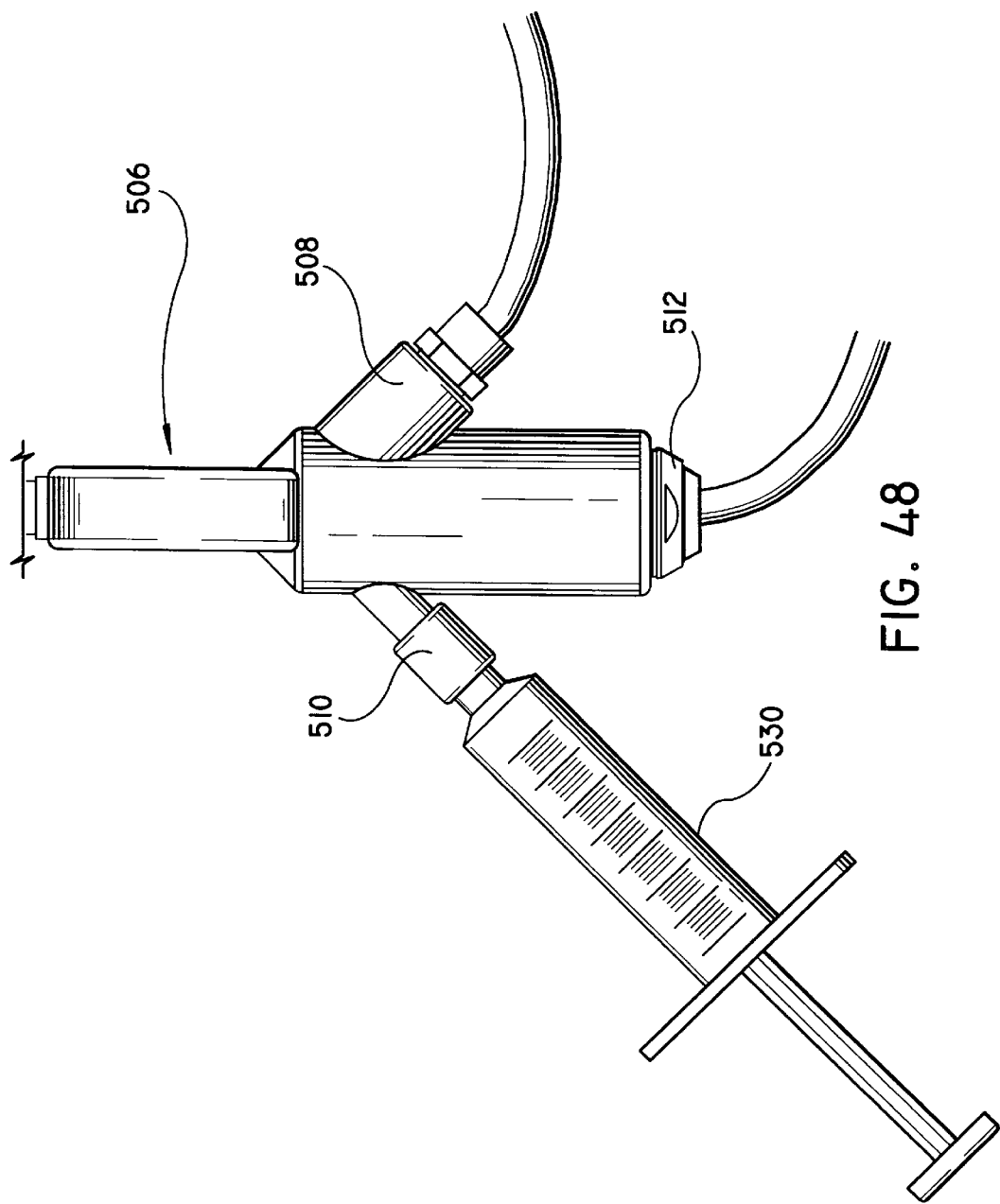

APPARATUS FOR THERMAL TREATMENT OF TISSUE

BACKGROUND

1. Technical Field

The present disclosure relates generally to a method and apparatus for thermal treatment of tissue and, more particularly, to an auxiliary apparatus to be used with a conventional endoscope to provide the endoscope with thermal treatment capabilities. The auxiliary apparatus is particularly contemplated for use with a cystoscope or a urethroscope for hyperthermia treatment of prostatic tissue.

2. Background of the Related Art

Benign prostate hyperplasia (BPH) or hyperplasia affects over one out of every two males over the age of fifty. BPH is the non-cancerous enlargement of the prostate gland and is characterized generally by a constriction of the urethra by the prostate gland. An array of symptoms are associated with BPH including frequent urination, complications in urinary flow and associated pain.

Generally there are two primary methods for treating BPH, namely, drug therapy and surgical intervention. Drug therapy incorporates the use of one or more drugs such as Proscar™ and Hydrin™ to either reduce the size of the prostate or to relax the urethral muscles thereby facilitating the normal functioning of the urinary system. Known drug therapies, however, are limited in their effectiveness and present many drug side effect concerns.

Surgical methods for treating BPH include transurethral resection of the prostate (TURP), transurethral incision of the prostate (TUIP), visual laser assisted prostatectomy (VLAP), balloon dilation and stenting. TURP is the most common method employed for BPH treatment today and involves the insertion of an electrosurgical cutting instrument through the urethral passage. The cutting elements of the instrument are positioned adjacent the prostate gland, and the instrument is energized such that the cutting elements selectively cauterize and resect tissue from the core of the prostate. The TURP procedure, however, has many side effects including bleeding, retrograde ejaculation, impotence, incontinence, edema and a prolonged recovery period for the patient. An example of an electrosurgical cutting instrument utilized in conjunction with a TURP procedure is disclosed in U.S. Pat. No. 5,192,280.

Transurethral incision of the prostate (TUIP) involves the use of an electrocautery device which is passed through the urethra. The device is employed to make multiple incisions in the prostate, thereby permitting the prostate to be displaced from the urethra wall to create an opening for urine flow. Success with the TUIP procedure is generally limited providing only temporary relief and requiring a subsequent repeat of the procedure in the future.

Visual laser assisted prostatectomy (VLAP) includes insertion of a laser catheter through the urethra and directing laser energy laterally through the catheter sleeve at the urethral wall and the prostatic tissue. The laser energy causes the tissue to coagulate. The coagulated tissue eventually necrosis from lack of blood flow and is naturally removed from the body. Drawbacks of VLAP include increased recovery time, acute pain and irritation, and undesired burning of the urethral wall. Examples of methods and apparatuses utilized in VLAP treatment of BPH are disclosed in U.S. Pat. No. 5,242,438 to Saadatmanesh et al. and U.S. Pat. No. 5,322,507 to Costello.

Balloon dilation procedures for BPH involve expanding and stretching the enlarged prostate with a balloon catheter to relieve pressure off the constricted urethra while stenting incorporates the insertion of tiny wire-mesh coils which expand into a scaffold to hold the urethra open. Balloon dilation and stenting, however, are only temporary procedures typically requiring follow up within a year period. In addition, stenting presents complications of stent migration and consequent irritation.

Transurethral microwave therapy (TUMT) and high intensity focused ultrasound (HIFU) have been developed for the treatment of BPH. In accordance with a TUMT procedure, a foley-type urethral catheter having a microwave emitting antenna at a probe end is inserted into the urethral passage for a period of time sufficient to treat the tissue by microwave radiation. Intraurethral applicators of this type are described in U.S. Pat. Nos. 4,967,765, 5,234,004 and 5,326,343. The drawbacks of TUMT include the inability to focus the heat energy in the prostatic area and the inability to achieve high temperatures uniformly within the prostate.

High intensity focused ultrasound (HIFU) includes directing high intensity ultrasound waves at the prostate tissue to create heat in a precise area to coagulate and necrose tissue. A transurethral probe is utilized to create the ultrasound beams for both imaging and ablation of the prostatic tissue. Disadvantages of this procedure include the inability to directly focus the ultrasound energy at the prostatic tissue.

A more recent form of treatment for BPH involves thermally treating prostatic tissue with radio frequency electromagnetic energy. For example, one current technique, known as transurethral needle ablation (TUNA™), involves the transurethral application of a medical instrument having a built-in RF needle electrode system. The TUNA™ instrument is inserted into the urethra and advanced to a position adjacent the prostate. Thereafter, the RF needles are advanced to penetrate the urethral wall and access the prostatic tissue. The RF system is activated whereby a RF current is transmitted through each electrode to pass through the tissue to a grounding pad thereby forming a necrotic legion which is eventually absorbed by the body. Apparatuses and methods for treating BPH via the TUNA™ technique are disclosed for example in U.S. Pat. No. 5,366,490.

The TUNA technique has several disadvantages which detract from its usefulness. In particular, the TUNA instruments are generally complex typically incorporating built in optical systems, aspiration systems, etc. As a result, the instruments are relatively expensive to manufacture. Moreover, the TUNA instruments are generally enlarged by virtue of the various systems incorporated within the instrument, thus, increasing patient trauma and discomfort during use.

Accordingly, the present disclosure is directed to an auxiliary apparatus for the RF thermal treatment of prostatic tissue. This apparatus is intended for use in conjunction with a conventional endoscope such as a cystoscope and incorporates an RF system and associated mechanism that is at least partially positionable within the working channel of the scope. The apparatus by use in conjunction with a conventional cystoscope makes use of the existing systems, e.g., optical and illumination, of the scope, which effectively results in a less complex and less expensive RF thermal treatment device. Furthermore, the apparatus may be used in cystoscopes as small as 5 mm (or even smaller) in diameter thereby providing a less invasive system for transurethral ablation as compared to the TUNA instruments and technique.

SUMMARY

An auxiliary electromagnetic thermal treatment apparatus for use with an endoscope to provide the endoscope with electromagnetic thermal treatment capabilities is provided. The auxiliary apparatus includes a handle portion and an elongate portion connected to the handle portion and dimensioned to be at least partially inserted within a working channel of an endoscope. The elongate portion includes at least one delivery tube having a memory portion comprised of a shape memory material and defining a normally unstressed curved configuration. The one delivery tube is longitudinally moveable relative to the handle portion to extend the memory portion beyond the working channel of the endoscope such that the memory portion assumes the normal unstressed curved configuration thereof. An electromagnetic probe is disposed within the delivery tube and is longitudinally moveable relative to the delivery tube to extend a probe end portion thereof beyond the delivery tube and within tissue. The electromagnetic probe is adapted to follow the curved configuration of the memory portion of the delivery tube for deployment at an angularly oriented relation with respect to the endoscope. A rotatable control member is mounted to the handle portion and operatively connected to the delivery tube. The control member is rotatable to move the delivery tube between a first retracted position and a second advanced position. An actuator is also mounted to the handle portion and is operatively connected to the electromagnetic probe. The actuator is moveable to extend the probe end portion beyond the delivery tube.

The present disclosure is also directed to a combination of an endoscope and an auxiliary thermal treatment device. A method for thermally treating tissue is also disclosed.

BRIEF DESCRIPTION OF THE DRAWINGS

Preferred embodiment(s) of the present disclosure are described herein with reference to the drawings wherein:

FIG. 1 is a perspective view of the auxiliary apparatus for thermal treatment of tissue in accordance with the principles of the present disclosure;

FIG. 2 is a cross-sectional view taken along the lines 2—2 of FIG. 1 illustrating the outer sleeve, the probe delivery unit disposed within the outer sleeve and the electrodes disposed within the delivery tubes of the delivery unit;

FIG. 3 is a side elevational view of the probe delivery unit;

FIG. 4 is an axial view of the probe delivery unit as viewed from its proximal end;

FIG. 5 is an axial view of the probe delivery unit as viewed from its distal end;

FIG. 6 is a top elevational view of the probe delivery unit;

FIG. 6A is a perspective view of the distal end of the probe delivery unit;

FIG. 7 is a side elevational of the handle of the apparatus of FIG. 1;

FIG. 8 is a cross-sectional view taken along the lines 8—8 of FIG. 7;

FIG. 9 is a cross-sectional view taken along the lines 9—9 of FIG. 7;

FIG. 10 is a top cross-sectional view of the handle illustrating the first and second actuators of the handle;

FIG. 10A is an isolated view illustrating connection of the probe delivery unit to the first actuator;

FIG. 11 is a side cross-sectional view of the handle further illustrating the connection of the second actuating member to the electrodes;

FIG. 12 is a view illustrating insertion of a cystoscope with mounted auxiliary thermal treatment apparatus within the urethral passage of the patient;

FIG. 13 is a cross-sectional view taken along the lines 13—13 of FIG. 12 illustrating the apparatus of FIG. 1 positioned within the working channel of the cystoscope;

FIG. 23 is a side plan view of the apparatus with the handle in cross-section;

FIG. 24 is a perspective view of the distal end of the elongate portion of the apparatus;

FIG. 30 is a side plan view of the distal end of the directional tube with portions cut away to depict a second thermocouple for detecting the temperature of tissue adjacent the treatment area;

FIG. 31 is a cross-sectional view taken along the lines 31—31 of FIG. 30;

FIG. 32 is a view illustrating insertion of a cystoscope and mounted thermal treatment apparatus within the urethral passage with the directional tube partially deployed;

FIG. 33 is a view illustrating the cystoscope and mounted apparatus inserted within the urethral passage with the directional tube fully deployed;

FIG. 34 is an enlarged view further illustrating the directional tube deployed;

FIG. 35 is a view similar to the view of FIG. 33 illustrating the electrode assembly deployed beyond the directional tube and penetrating the prostatic tissue;

FIG. 36 is an isolated view further illustrating the electrode assembly deployed within the prostatic tissue;

FIG. 40 is a side plan view of the electrode and directional tube with the directional tube partially cut-away to illustrate a second thermocouple for detecting the temperature of the tissue adjacent the treatment area;

FIG. 41 is a cross-sectional view taken along the lines 41—41 of FIG. 40;

FIG. 42 is a side plan view of another alternate embodiment of the auxiliary thermal treatment apparatus incorporating a dissipating agent for facilitating transfer of the electromagnetic energy to the treated tissue;

FIG. 43 is a view taken along the lines 43—43 of FIG. 42 depicting components of the handle of the apparatus of FIG. 42;

FIG. 45 is a side plan view of the distal end of the elongate portion with portions of the directional tube and the electrode assembly cut-away;

FIG. 46 is a cross-sectional view taken along the lines 46—46 of FIG. 45;

FIG. 47 is a cross-sectional view taken along the lines 47—47 of FIG. 45;

FIG. 48 is a plan view of the handle illustrating a syringe connected to the handle;

DETAILED DESCRIPTION OF PREFERRED EMBODIMENTS

Figure 16:
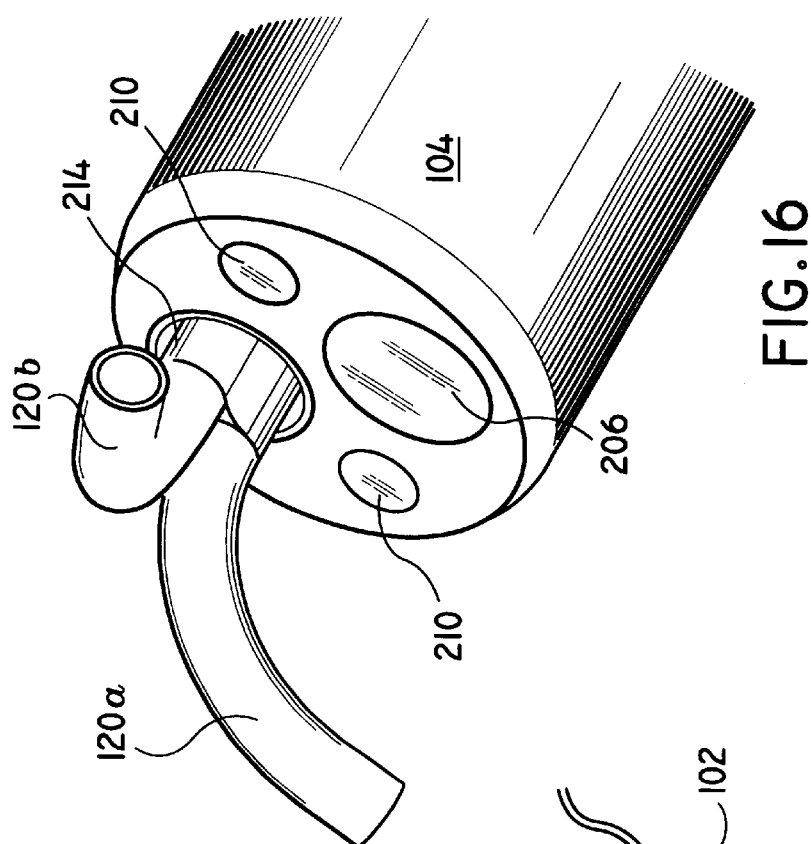
FIG. 16 is a view similar to the view of FIG. 14 illustrating deployment of the distal end of the delivery tubes of the probe delivery unit whereby the distal end assumes its normal unstressed condition angularly oriented relative to the longitudinal axis of the apparatus.

The apparatus of the present disclosure is intended to deliver electromagnetic energy to tissue for thermal treatment of the tissue including tissue ablation, tissue vaporization and/or tissue coagulation. The apparatus has particular application in the treatment of benign prostate hyperplasia (BPH) with electromagnetic radio frequency (RF) energy, however, it is to be appreciated that the apparatus is not limited to such application. For example, the apparatus is not limited to the treatment of BPH, but, may be used in other surgical procedures such as cardiac ablation, cancer treatment, etc. Moreover, the apparatus may be used in any minimally invasive procedure where thermal treatment of tissue is desired and access to the tissue is limited.

The apparatus is particularly intended to be used in conjunction with an endoscope such as a cystoscope, fiber scope, laparoscope, urethroscope, etc. to provide the scope with thermal treatment capabilities. More specifically, the apparatus is at least partially insertable within the working channel of an endoscope, which is positioned in the body to access a targeted tissue area, to thermally treat the desired tissue.

Referring now to FIGS. 1–2, apparatus 100 includes handle 102 and elongate body 104 connected to the handle 102 and extending distally therefrom. Handle 102 includes frame 106 which is preferably fabricated from a suitable rigid polymeric material or, in the alternative, from stainless steel or an aluminum alloy. Frame 106 is advantageously dimensioned to be grasped by the hands of the surgeon. Handle 102 further includes first and second actuators 108, 110 which are mounted for movement relative to the frame 106 to operate the apparatus.

Elongate body 104 may include outer sleeve 112 preferably fabricated from a flexible material such as Nitinol. It is envisioned that outer sleeve 112 may alternately be rigid if, for example, it is intended to be used with a rigid scope. Outer sleeve 112, if provided, ranges from about 25 to about 40 millimeters (mm) in length, preferably, about 37 mm and ranges from about 1.5 to about 2.5 millimeters in diameter, preferably about 2.3 mm. Outer sleeve 112 defines axial bore 114 extending therethrough. Other dimensions are also contemplated. Alternatively, the outer sleeve may be eliminated.

Referring now to FIGS. 2–6A, in conjunction with FIG. 1, probe delivery unit, identified generally by reference numeral 116, is disposed within axial opening 114 of outer sleeve 112. Probe guide 116 is adapted for reciprocal longitudinal movement within the opening 114 and includes first and second hollow delivery (directional) tubes 118a, 118b. Delivery tubes 118a, 118b are preferably connected to each other for a major portion of their respective lengths, but are separated at the distal end portions 120a, 120b as best depicted in FIGS. 6 and 6A. Delivery tubes 118a, 118b accommodate electromagnetic probes 122 therein (FIG. 2) and function in guiding the probes 122 at desired orientations within the tissue.

Referring particularly to FIGS. 3–6A, delivery tubes (or catheter) 118a, 118b of probe guide 116 are preferably fabricated from a shape memory metal such as NITINOL and are preferably joined to each other by welding or with the use of adhesives. In the normal condition of delivery tubes 118a, 118b, the distal ends 120a, 120b of the tubes 118a, 118b each assume the arcuate configuration depicted in FIGS. 3–6A, i.e., the distal end portions 120a, 120b have memory to define the arcuate orientation as shown, thus, providing arcuate paths for electromagnetic probes 122 to follow to penetrate the tissue. The particular orientation of memory portions 120a, 120b of delivery tubes 118a, 118b can be varied depending on the objectives of the surgical procedure. The distal end or memory portions 120a, 120b of delivery tubes 118a, 118b readily adapt a linear configuration when confined in the outer sleeve 112 of elongated portion 104 as will be discussed.

In a preferred embodiment (e.g., in BPH application), memory portions 120a, 120b of delivery tubes 118a, 118b define a radius of curvature "r" ranging between about 0.250 to about 0.400 inches, preferably about 0.312 inches. Memory portions 120a, 120b are also separated by an angle "T" ranging from about 45• to about 90• (degrees). Clearly other dimensions and angular orientations of memory portions 120a, 120b are contemplated as well.

With reference again to FIG. 2, electromagnetic probes 122 disposed within delivery tubes 118a, 118b include bipolar electrodes formed of a thin solid wire capable of carrying an electromagnetic radiofrequency (RF) current. The electrodes are relatively flexible to follow along the path defined by delivery tubes 118a, 118b, but, sufficient in rigidity to be advanced into tissue. The electrodes are preferably made of Nitinol so they can return to their normally straight configuration after being bent by the delivery tubes. The electrodes each have a pointed tip to facilitate penetration through the tissue. Each electrode has an insulating layer, designated by reference numeral 124, which extends along a major portion of its length to prevent damage to non-targeted body tissue. Each electrode is therefore electrically isolated from its delivery tube. Insulating layer 124 terminates to expose the distal penetrating portions of the electrodes 122, thus, permitting the transmission of electromagnetic RF current to the targeted body tissue. Alternatively, monopolar electrodes could be provided.

Referring now to FIGS. 7–11, probe unit 116 extending through outer sleeve 112 is operatively connected to first actuator 108. In a preferred arrangement, first actuator 108 includes an inner recess 125 which receives the proximal end of probe guide 116 in interfitting relation as depicted in FIG. 10A. Other mounting arrangements for connecting actuator 108 and probe guide 116 are envisioned as well such as the use of adhesives, screws, or the like. Longitudinal movement of first actuator 108 causes corresponding longitudinal movement of probe delivery unit 116 within outer sleeve 112. That is, first actuator 108 is moveable to cause reciprocal movement of probe guide 116 between a first retracted position where the distal end or memory portions 120a, 120b of guide 118a, 118b are contained within outer sleeve 112 and a second advanced position where the memory portions 120a, 120b extend beyond the distal end of outer sleeve 112 and assume their angularly oriented positions as will be discussed hereinbelow.

Second actuator 110 is operatively connected to electromagnetic probes 122 disposed within delivery tubes 118a, 118b. Any conventional means appreciated by one skilled in the art for connecting actuator 110 to electromagnetic probes 122 may be utilized. In the preferred embodiment, an interfitting relationship of the proximal ends of electromagnetic probes 122 with an inner recess of second actuator 110 (such as the arrangement disclosed above with first actuator 108) will be employed. Second actuator 110 is moveable to cause corresponding motion of electromagnetic probes 122 within their respective delivery tubes 118a, 118b to extend the penetrating end portions of the probes 122 beyond the tubes for deployment into tissue.

As seen in FIGS. 7, 10 and 11, a pair of conductive wires 126 are provided to connect electromagnetic probes 122 to coupling 128 mounted to handle 104. Coupling 128 is connectable to an external radio frequency energy source "s" as schematically depicted in FIG. 1.

Referring now to FIG. 12, apparatus 100 is shown positioned within a conventional cystoscope 200 for thermal treatment of prostrate "p" to alleviate the symptoms of BPH. One conventional cystoscope 200 with which the apparatus of the present disclosure can be utilized is the ACN Flexible CystoNephroscope manufactured by Circon ACMI. Cystoscope 200 includes handle 202 and a flexible elongated portion 204 connected to the handle 202 and extending distally therefrom. Cystoscope 200 incorporates an optical system to permit viewing of the tissue to be treated. As depicted in FIG. 13, the optical system preferably consists of flexible fiber optic bundles (identified by reference numeral 206) which are accommodated within a longitudinal bore extending through the elongated portion 204 of the scope 200. The fiber optic bundles 206 extend to eyepiece 208 where the surgeon can view the image transmitted by the optical system.

Cystoscope 200 also includes an illumination system which provides illuminating light to the targeted tissue area. The illumination system includes a plurality of optical fibers 210 which are accommodated within a plurality of longitudinal channels (two are shown) of elongated portion 204 and extend within handle 202 where they terminate at illumination coupler 212. Illumination coupler 212 is connectable to a conventional light source as is known in the art. Cystoscope 200 further includes a working channel 214 extending through flexible elongated portion 204 and terminating at channel port 216 of handle 202. Working channel 214 is adapted to receive various surgical instrumentation through channel port 216 (e.g., thermal treatment apparatus 100) to permit the performance of surgical procedures at the distal end of the cystoscope 200. Cystoscope 200 is preferably a 5 mm scope.

OPERATION

The use of apparatus 100 with cystoscope 200 in conjunction with the thermal treatment of prostatic tissue will now be discussed. Cystoscope 200 is inserted through urethral passage "u" of the patient and advanced within the passage until the distal end of the scope is adjacent prostate gland "p". Thereafter, elongate body 104 of apparatus 100 is inserted into working channel 214 of cystoscope 200 and advanced into the working channel 214 until handle 102 of the apparatus contacts channel port 216 of scope handle 202. As an alternative method of insertion, apparatus 100 may be positioned within cystoscope 200 prior to insertion within the urethral passage "u" and the entire assembly may be then advanced within the urethral passage. It is envisioned that handle 102 of apparatus 100 may incorporate a locking mechanism to lockingly engage channel port 216 of handle 202 of the cystoscope 200.

Figure 15:
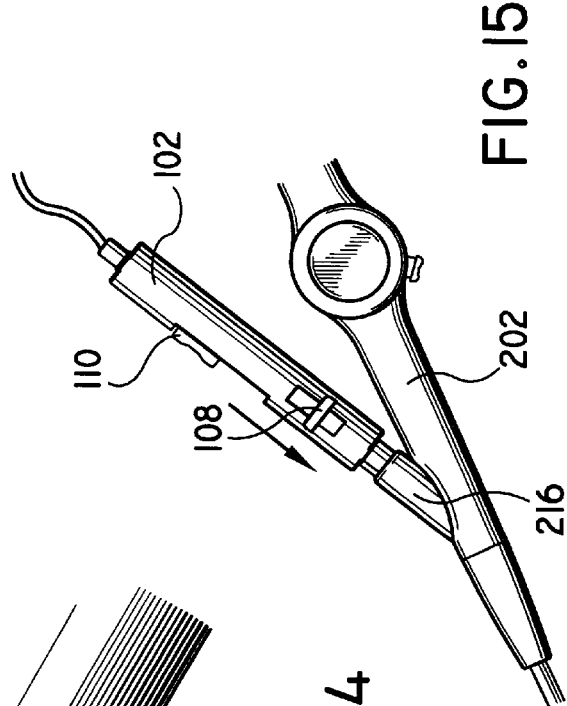
FIG. 15 is a view illustrating distal movement of the first actuator to deploy the distal end portion of the delivery tubes of the probe delivery unit.
Figure 14:
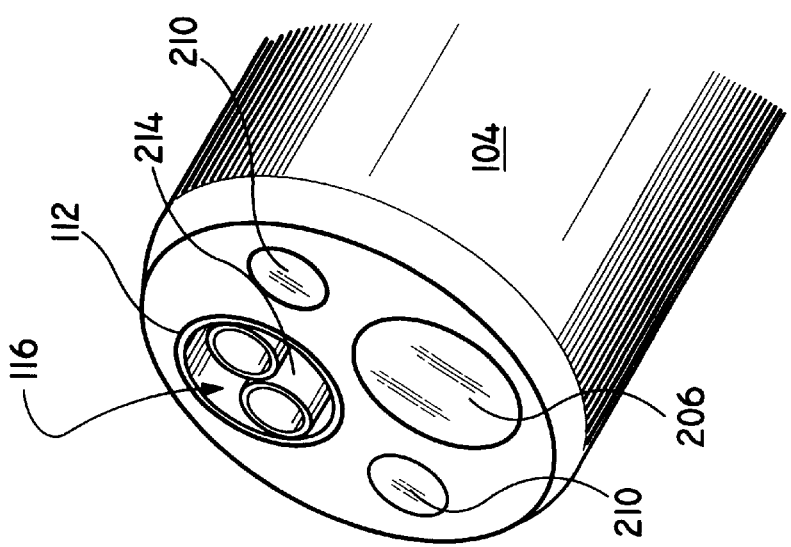
FIG. 14 is an enlarged perspective view of the distal end portion of the cystoscope illustrating the delivery tubes of the probe delivery unit contained within the working channel of the scope.

With reference now to FIG. 14, probe delivery unit 116 is shown in its retracted position. In such position, the distal end portions 120a, 120b of delivery tubes 118a, 118b are constrained by outer sleeve 112 (and elongated portion 204 of scope 200) thereby assuming a general linear configuration within the sleeve 112. Thereafter, first actuator 108 is distally advanced as depicted in FIG. 15 to move probe delivery unit 116 from its retracted position of FIG. 14 to its extended position of FIG. 16. Upon exiting working channel 214 of cystoscope 200, the distal ends or memory portions 120a, 120b of delivery tubes 118a, 118b are no longer constrained by outer sleeve 112, and, thus are free to assume their normal unstressed curved configurations depicted in FIG. 16 and FIG. 16A. By exiting through the distal end face of the working channel 214 of cystoscope 200, the deployment of delivery tubes 118a, 118b can be monitored with the optical system of cystoscope 200. That is, both 0 degree and oblique viewing is achieved. In the extended position of delivery tubes 118a, 118b, the distal end portions 120a, 120b may slightly extend beyond the outer circumference of scope 200, but, however, do not penetrate the urethral lining. It is to be noted that the degree of deployment of memory portions 120a, 120b of delivery tubes 118a, 118b may be selected to thereby achieve desired angular orientations of the memory portions 120a, 120b, consequently, controlling the orientation of the deployed electrodes. (As noted above, alternately, outer sleeve 112 need not be provided and the apparatus is advanced through the working channel to expose the delivery tubes.)

Figure 17:
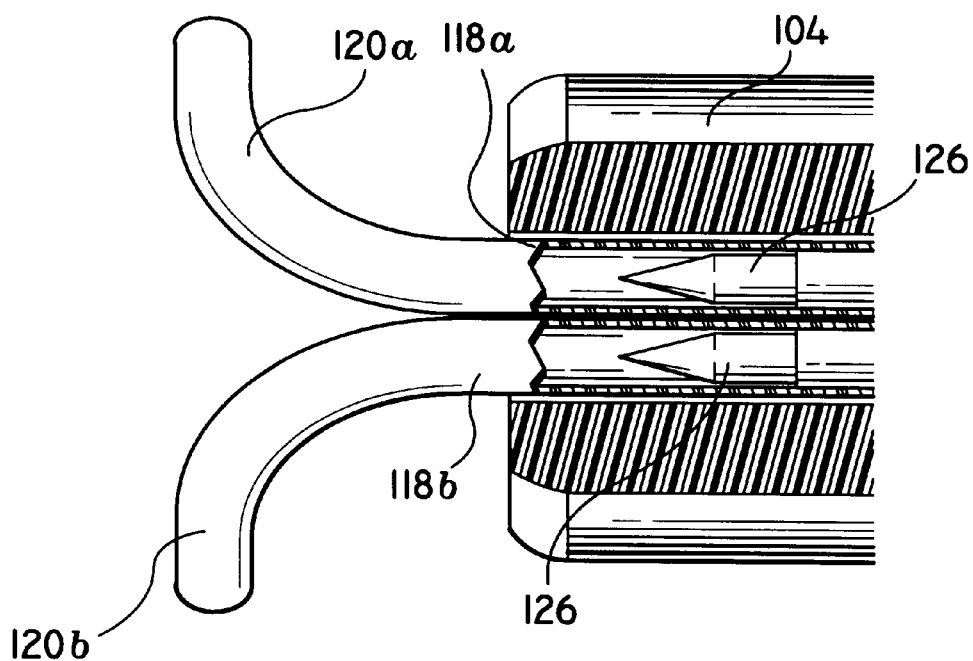
FIG. 17 is a side plan view of the distal end of the cystoscope in partial cross-section further illustrating deployment of the delivery tubes with the electrodes in a retracted position disposed within the tubes.
Figure 18:
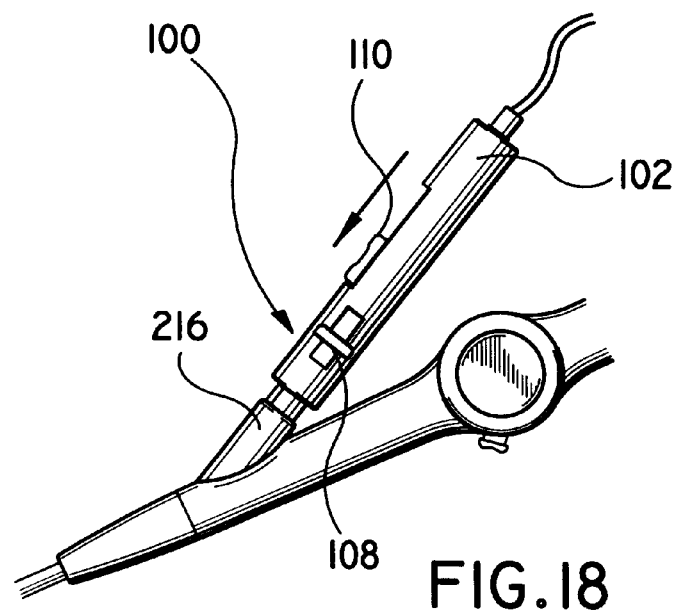
FIG. 18 is a view similar to the view of FIG. 15 illustrating distal movement of the second actuating member to advance the electrodes through the delivery tubes of the probe delivery unit and within the patient's prostatic tissue.
Figure 19:
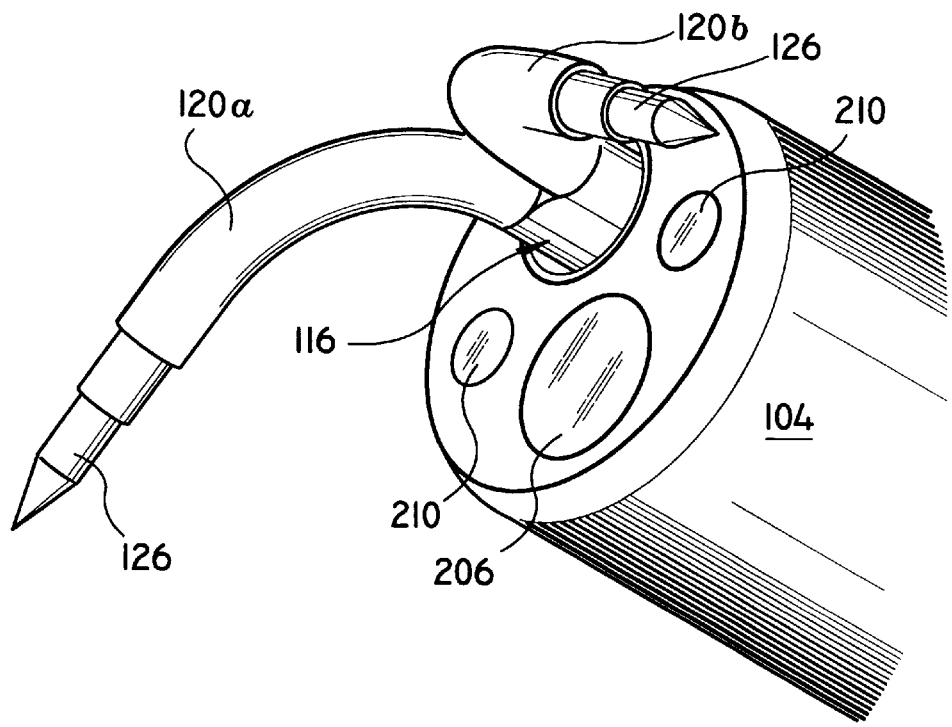
FIG. 19 is a view similar to the view of FIG. 16 illustrating the electrodes in the advanced position.

Referring now to FIGS. 17–19, with distal end portions 120a, 120b in their extended positions, attention is directed to deploying the electromagnetic probes 122. FIG. 17 depicts the electromagnetic probes 122 in their retracted position within delivery tubes 118a, 118b. Second actuator 110 is selectively distally advanced to advance electromagnetic probes 122 from delivery tubes 118a, 118b as depicted in FIG. 18. During advancing movement, the penetrating end portions 126 of probes 122 flex or bend to conform to the curved configuration of memory portions 122a, 122b of the delivery tubes 118a, 118b to pierce the urethral wall "u" and enter the prosthetic tissue "p". The degree of deployment of electromagnetic probes 122 may be selectively controlled (e.g., partial deployment) with second actuator 110 to thereby provide a level of control over the thermal treatment field generated by the probe.

The system is then energized to thermally treat (e.g., ablate, vaporize or cauterize) the desired prosthetic tissue with RF energy. As a result of this treatment, the prosthetic tissue BPH necroses and dies, thus, relieving pressure off the urethral wall and alleviating the symptoms of BPH. During treatment, the depth of penetration of penetrating end portions 126 of electromagnetic probes 122 may be selectively adjusted by movement of second actuator 110 to permit specific regions of the prosthetic tissue "p" to be targeted for thermal treatment thus providing heating pattern flexibility and control. During treatment, insulating layer 124 of electromagnetic probes 122 preferably contact the urethral wall "u" to prevent damage to the wall.

Upon completion of the procedure, the system is de-energized and the cytoscope 200 and apparatus are removed from the urethral passage "u".

Figure 20:
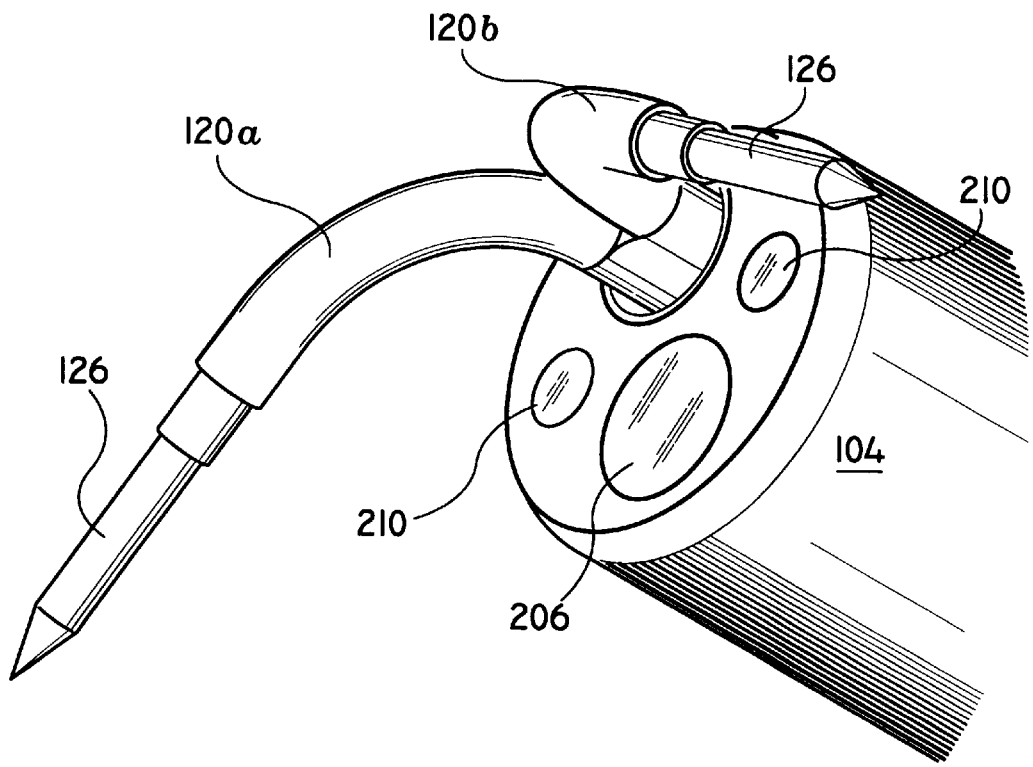
FIG. 20 is a view of an alternate embodiment of the auxiliary thermal treatment apparatus where a greater portion of the electrode is exposed to provide an increased thermal treatment capacity.

FIG. 20 is a perspective view of the distal end of cystoscope 200 with an alternate auxiliary thermal treatment apparatus mounted within the working channel 214 (FIG. 13) of the scope. This thermal treatment apparatus is identical to the apparatus described in connection with FIG. 1 except that in accordance with this embodiment, a greater portion or length of the inner electromagnetic probe 122 is exposed (i.e., uninsulated) to increase the thermal treatment region generated by the probes (Compare with FIG. 19). It is to be appreciated that the lengths of the exposed electrode portions i.e. the length of insulation, may be varied to achieve desired thermal treatment objectives.

Figure 21:
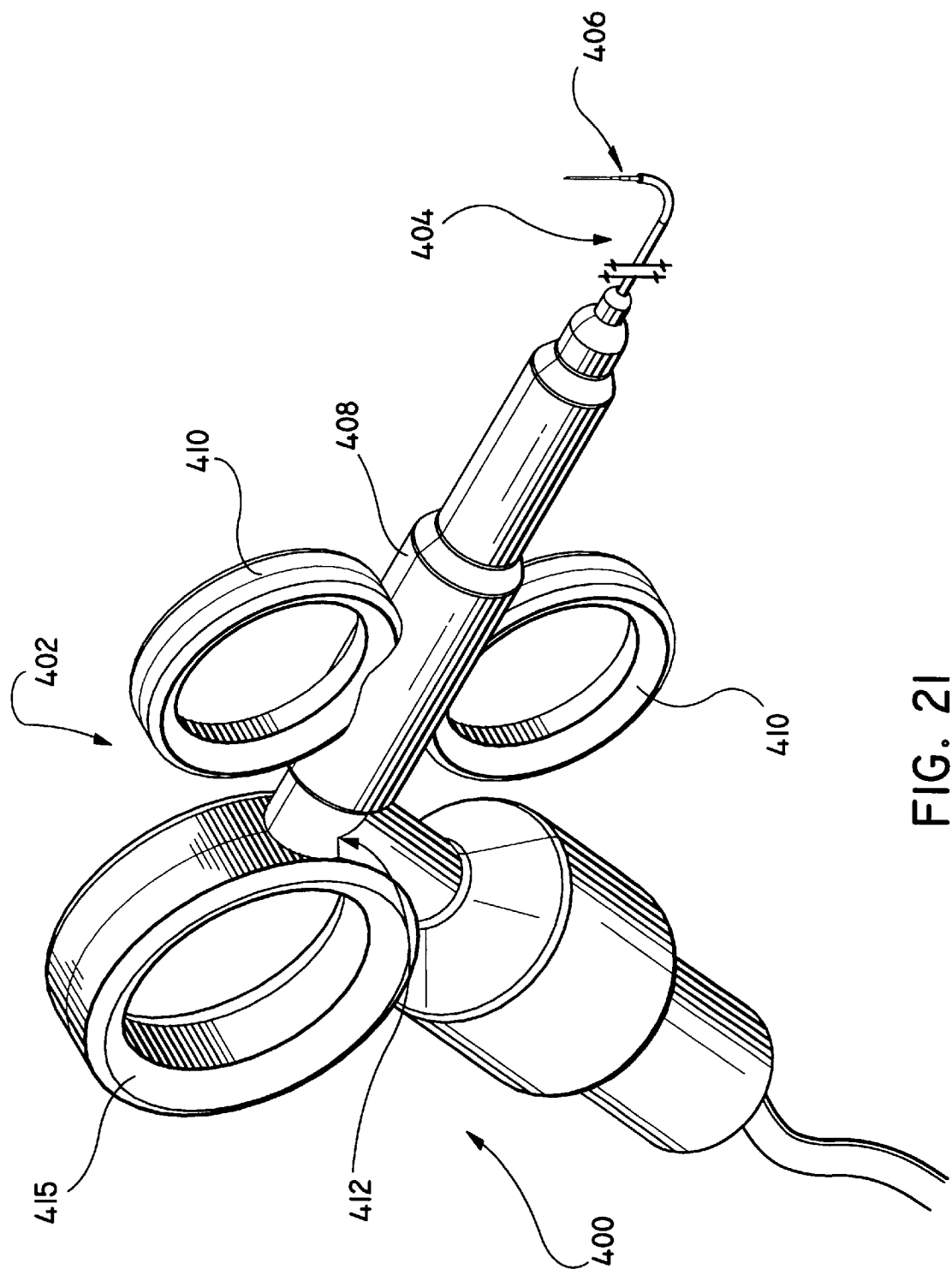
FIG. 21 is a perspective view of another alternate embodiment of the auxiliary apparatus for thermal treatment of tissue incorporating a coaxial arranged bipolar electrode assembly.
Figure 22:
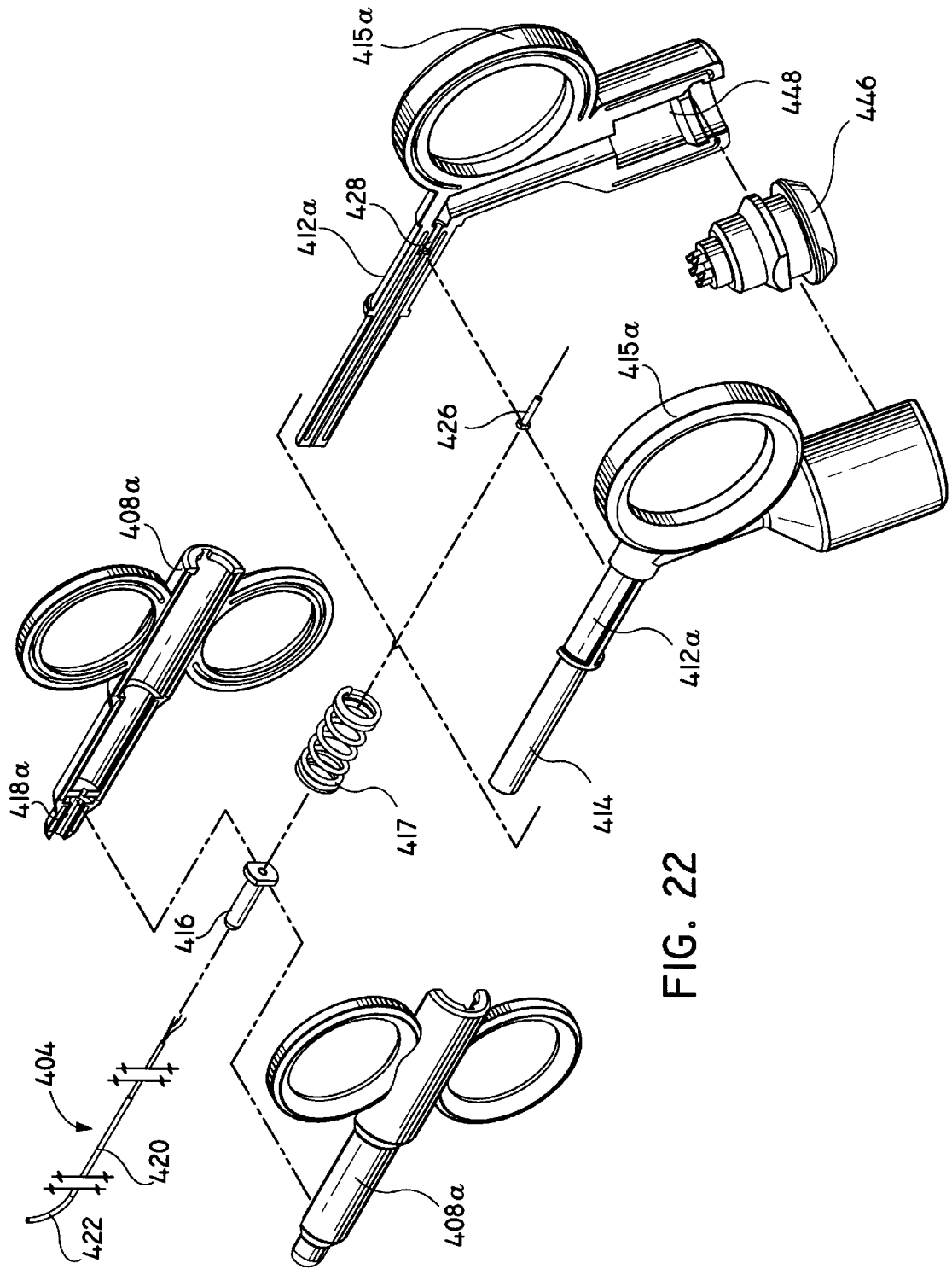
FIG. 22 is a perspective view with parts separated of the auxiliary apparatus of FIG. 21.

Referring now to FIGS. 21–23, there is illustrated another alternate embodiment of the auxiliary RF thermal treatment apparatus of the present disclosure. Apparatus 400 includes housing or handle 402, elongate portion 404 connected to the handle and extending distally therefrom, and a bipolar or monopolar electrode unit 406 which extends beyond the distal end of the elongate portion 404. Handle 402 includes frame 408 defining a generally cylindrical configuration and having diametrically opposed finger rings 410 mounted thereto. Finger rings 410 accommodate the fingers of the user to facilitate holding and manipulation of the apparatus 400. Handle 402 further includes actuating portion 412 which is mounted to frame 408.

Actuating portion 412 includes a distal inner cylindrical mounting section 414 which is received within an internal bore of frame 408 to mount the actuating portion 412 to frame 408. Mounting section 414 is dimensioned to slide within frame 408 thereby permitting relative movement between the two components, i.e., actuating portion 412 is reciprocally moveable relative to frame 408 to operate the apparatus as will be discussed. Actuating portion 412 further includes a thumb ring structure 415 for accommodating the thumb of the user. A coil spring 417 mounted about mounting section 414 to normally bias the actuating portion 412 to a normal proximalmost position.

The components of handle 402 are preferably fabricated from a suitable rigid polymeric material or a metal such as stainless steel. The supporting components including frame 408 and actuating portion 412 preferably incorporate respective half sections 408a, 412a (FIG. 22) which are secured to each other about their peripheries with the use of adhesives, screws, etc.

Figure 27:
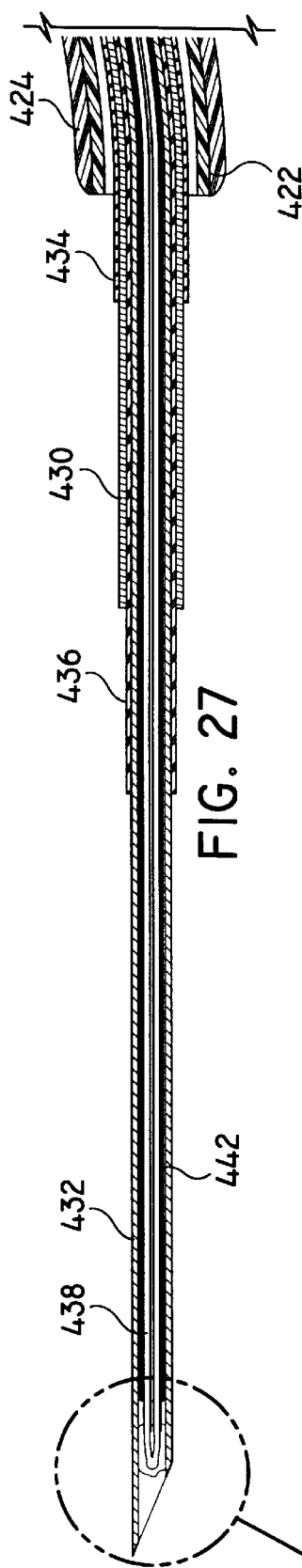
FIG. 27 is an enlarged cross-sectional view of the distal end of the electrode assembly and deployed beyond the directional tube.
Figure 27A:
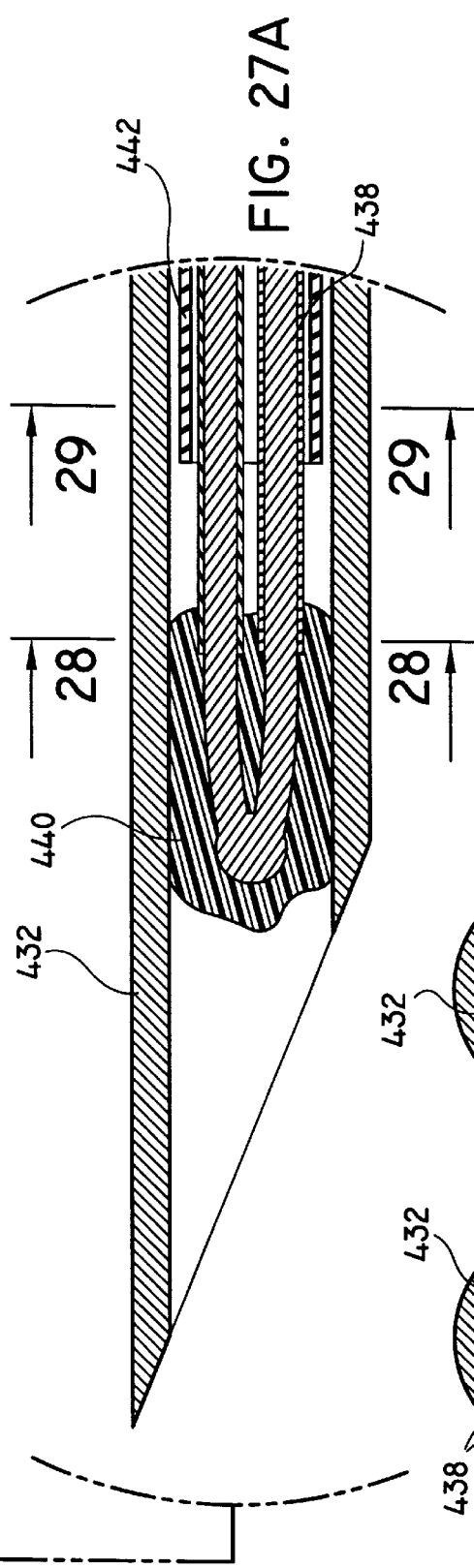
FIG. 27A is an enlarged isolated view of the distal tip of the electrode assembly with a thermocouple positioned therein for detecting the temperature at the treatment area.

Referring now to FIGS. 24–27, in conjunction with FIG. 22, elongate portion 404 is mounted to the distal end of frame 408 through ferrule 416 which is fixedly mounted within corresponding recesses 418 defined in frame 408 (FIG. 22). Elongate portion 404 includes outer delivery catheter 420. Outer delivery tube or catheter 420 is fabricated from a flexible material and has a shape memory portion 422 at its distal end. At its proximal end, delivery tube 420 is fixedly mounted to ferrule 416 by the use of adhesives, crimping, etc. Materials of fabrication for the shape memory portion 422 of delivery catheter 420 include Nitinol. Similar to the aforedescribed embodiment, in the normal unstressed condition of delivery catheter 420, memory portion 422 defines an arcuate orientation angularly oriented relative to the longitudinal axis as shown. In a preferred embodiment (e.g., in BPH application), memory portion 422 defines a radius of curvature "r" ranging between about 0.300 to about 0.500 inches, preferably about 0.400 inches. Delivery catheter 420 preferably has an outer diameter of about 0.48 inches. A Teflon™ shrink tubing 424 is preferably disposed about delivery tube 420 as best depicted in FIG. 27.

Bipolar electrode unit 406 is disposed within delivery catheter 420 and extends through handle 402 where it is connected to actuating portion 412 through ferrule 426. Ferrule 426 is fixedly mounted within a correspondingly dimensioned recess 428 (FIG. 22) formed in actuating portion 412. Through this arrangement, movement of actuating portion 412 causes corresponding translation of electrode unit 406 within delivery catheter 420.

Figures 25, 26:
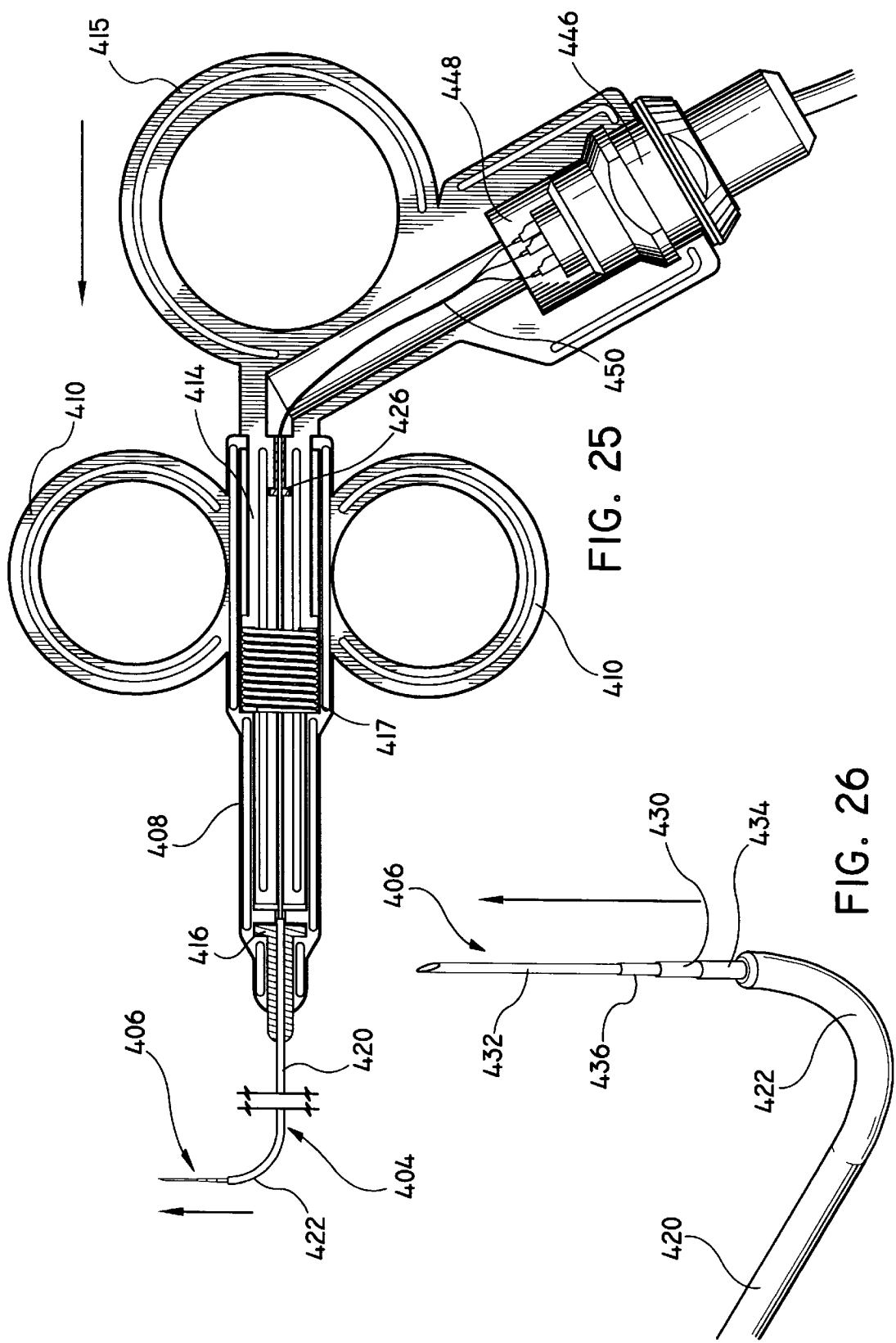
FIG. 25 is a view similar to the view of FIG. 23 illustrating actuation of the actuating portion to deploy the electrode assembly beyond the directional (delivery) tube of the elongate portion.
FIG. 26 is a view similar to the view of FIG. 25 further illustrating the electrode assembly deployed from the directional tube.

As best illustrated in FIGS. 26–27 which depict electrode unit or assembly 406 deployed via advancement of actuating portion 412, the electrode assembly 406 includes an outer tubular bipolar electrode 430 and an inner tubular bipolar electrode 432 coaxially mounted within the outer electrode 430. Inner bipolar electrode 432 extends distally beyond outer tubular electrode 430. Each electrode 430, 432 has insulating layers 434, 436 respectively. Inner electrode 432 is preferably a needle electrode having a sharpened penetrating end as shown.

Figure 29:
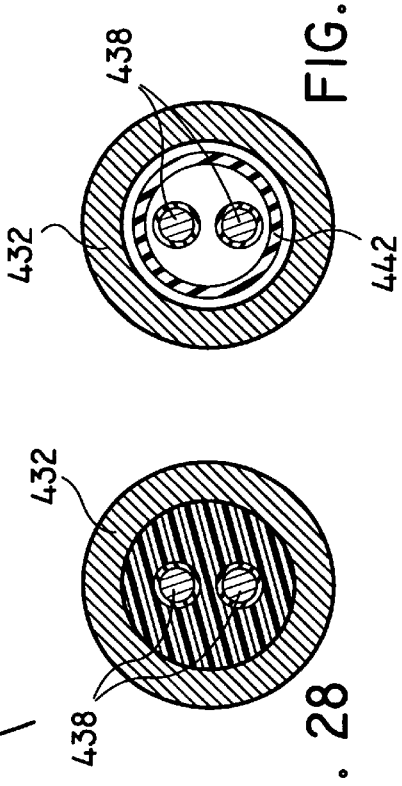
FIG. 29 is a cross-sectional view taken along the lines 29—29 of FIG. 27A.
Figure 28:
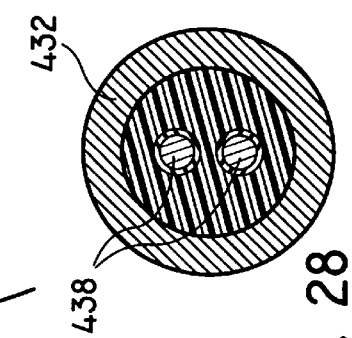
FIG. 28 is a cross-sectional view taken along the lines 28—28 of FIG. 27A.
Figure 37:
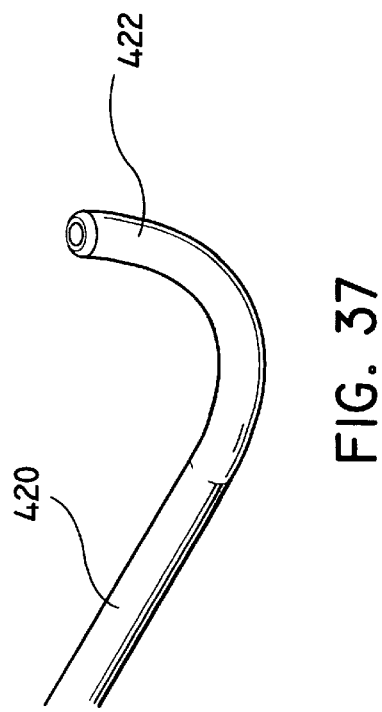
FIG. 37 is a view of an alternate embodiment of the auxiliary thermal treatment apparatus of FIG. 21 incorporating a monopolar electrode assembly.
Figure 38:
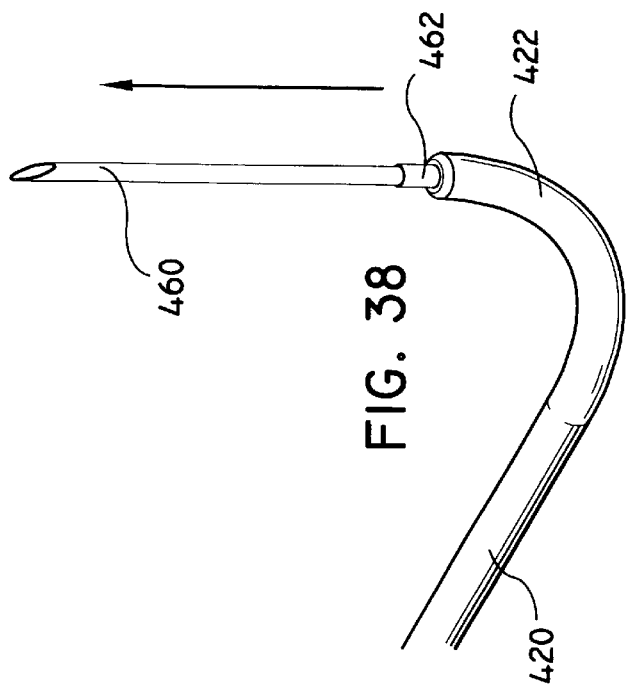
FIG. 38 is a perspective view of the distal end of the electrode assembly with the monopolar electrode deployed beyond the distal end of the directional tube.
Figure 39:
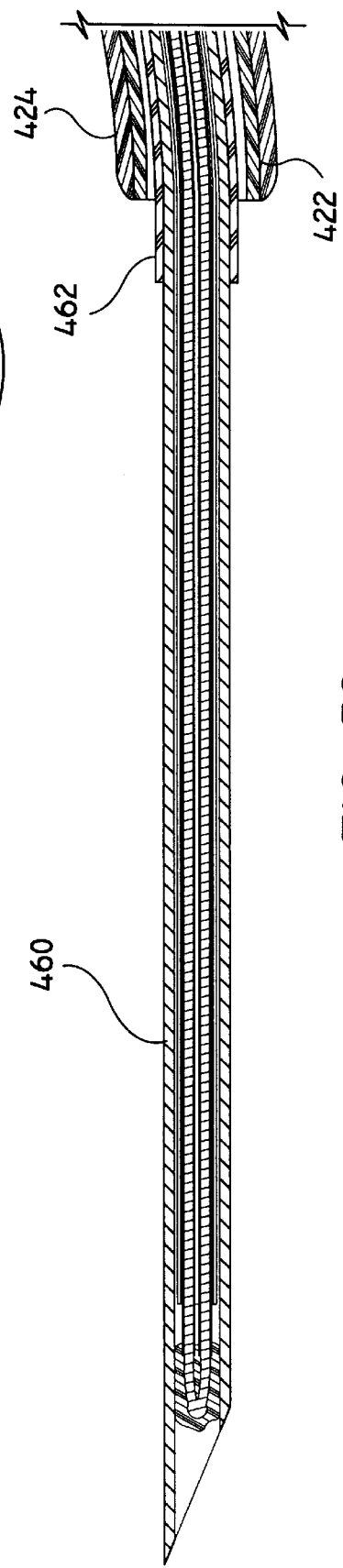
FIG. 39 is a cross-sectional view of the electrode illustrating a thermocouple disposed within the electrode for detecting the temperature of the treatment area.

Referring now to FIGS. 27–29, apparatus 400 further includes a first thermocouple 438 which extends within the axial bore of inner electrode 432. First thermocouple 438 is intended to measure the temperature of the tissue within the treatment area for monitoring purposes during the surgical procedure. An epoxy sealant 440 may be applied about the distal end of the thermocouple 438. First thermocouple 438 may be disposed within a protective sleeve 442 as shown. As depicted in FIGS. 30–31, a second thermocouple 444 may also be provided to measure the temperature of the tissue outside and adjacent the treatment area to ensure that this tissue is not undesirably thermally ablated. Second thermocouple 444 preferably extends between delivery catheter 420 and shrink tubing 424 which, as stated above, is wrapped about the outer surface of delivery catheter 420.

With reference again to FIGS. 22, 23 and 25, apparatus 400 further includes an electrical connector 446 which is mounted within a corresponding recess 448 in actuating portion 412 of handle 402. Connector 446 electrically connects the electrode assembly 406 and thermocouples 438, 444 to the RF energy source and the thermocouple accessory instrumentation, respectively, through appropriate wires 450. Accessory instrumentation contemplated for use with thermocouples 438, 444 include a digital monitor to provide a readout of the temperatures ascertained with the thermocouples.

Referring now to FIGS. 32–34, use of the apparatus 400 in connection with the thermal treatment of prostatic tissue to treat BPH will be discussed. Apparatus 400 is intended for use with a conventional scope such as cystoscope 200 which is identical to the cystoscope described hereinabove and is insertable within the working channel 214 of the scope through instrument port 216 (FIG. 13). In a preferred method of application, cystoscope 200 is initially inserted and advanced within the urethral passage "u" whereby the distal end of the scope is positioned adjacent the prostatic tissue to be treated. Auxiliary apparatus 400 is thereafter introduced through channel port 216 and advanced within working channel 214. Alternatively, the apparatus 400 can be inserted through the working channel port 216 and the working channel 214, and the entire assembly inserted into the urethral passage. It is to be noted that memory portion 422 of delivery catheter 420 assumes a generally linear configuration upon insertion within working channel 214 of the scope. Upon exiting the distal end of working channel 214, memory portion 422 assumes its normal unstressed curved orientation depicted in FIGS. 32–34. FIG. 32 illustrates memory portion 422 partially deployed while FIGS. 33–34 illustrate the memory portion 424 in the fully deployed position. As shown in FIG. 34, memory portion 422 will not penetrate the prostatic tissue upon deployment, but, rather will engage the inner wall of the urethra and bias the wall inwardly.

With reference now to FIG. 35–36, actuating portion 412 is then advanced in the direction of the directional arrow of FIG. 35 to advance the electrode assembly 406, i.e., actuating portion 412 is advanced from the position depicted in FIG. 23 to the position depicted in FIG. 25. Upon deployment, the needle portion of inner electrode 432 pierces the urethral wall "u" to access the prostatic tissue "p". Electrode unit 406 is continually advanced whereby outer electrode 430 is disposed within the prostatic tissue and insulating layer 434 of the outer electrode 430 is adjacent the urethral lining. The system is thereafter energized whereby a thermal treatment region is created by transfer of RF energy between the outer and inner electrodes 430, 432.

The coaxial arrangement of the electrode assembly 406 reduces the overall diameter of the elongate portion 404 of the thermal treatment apparatus, thus, facilitating incorporability within a cystoscope. It is to be appreciated that the arrangement and lengths of the exposed electrodes 430, 432 (and thus insulation) may be varied to create other thermal treatment capacities.

FIGS. 37–41 illustrate an alternate embodiment of the auxiliary thermal treatment apparatus of FIG. 20. This apparatus is similar in most respects to the apparatus of FIG. 20, but, incorporates a monopolar electrode assembly having a single monopolar electrode 460 with insulating layer 462. The apparatus may be utilized with a grounding pad positioned adjacent the body as is conventional in the art. Delivery catheter 420 and memory portion 422 are substantially similar to the prior embodiment. A shrink tubing 424 is positioned about delivery catheter 420. As best depicted in FIGS. 40–41, thermocouple 438 is disposed within delivery catheter 420 and thermocouple 444 is disposed between the shrink tubing 424 and the outer surface of delivery catheter 420.

Referring now to FIGS. 42–43, an alternate embodiment of the monopolar thermal treatment apparatus of FIGS. 37–41 is illustrated. Apparatus 500 includes handle portion 502 having frame 504 and actuating portion 506 slidably mounted to the frame. Actuating portion 506 includes dual connectors, namely, electrode connector 508 and infusion port 510. Electrode connector 508 connects to a RF energy source. Infusion port 510 is preferably a luer-type connector and operatively connects to an infusion liquid or dissipating agent utilized to facilitate dissipation of the RF energy at the electrode end. Actuating portion 506 further includes thermocouple connector 512 which connects to one of the thermocouples of the instrument. Frame 504 of handle portion 502 includes a separate thermocouple connector 514 mounted thereto which electrically connects with a second thermocouple incorporated in the instrument. Actuating portion 506 is slidably mounted to frame 504 and is connected to the electrode unit in an identical manner to that described above. The remaining components are identical to their corresponding parts described in connection with the embodiment of FIG. 21. In accordance with this embodiment, other than the hollow passage discussed below, the electrode unit is substantially identical to that described in connection with the aforedescribed embodiment of FIGS. 37–41.

As depicted in FIGS. 45–47, a first thermocouple 516 extends between the outer shrink tubing 518 and delivery catheter 520 and is utilized to measure the temperature of the tissue adjacent the treatment area. First thermocouple 516 is electrically connected to electrode connector 508 of actuating portion 506. A second thermocouple 522 extends between insulating layer 524 and monopolar needle electrode 526 to detect the temperature of the tissue within the treatment area. Second thermocouple 522 is electrically connected to electrode connector 514 of frame 504.

FIGS. 46–47 also illustrate the dissipating agent or fluid 528, e.g., saline solution, which passes through the hollow passage of the electrode 526 as will be discussed.

Figure 44:
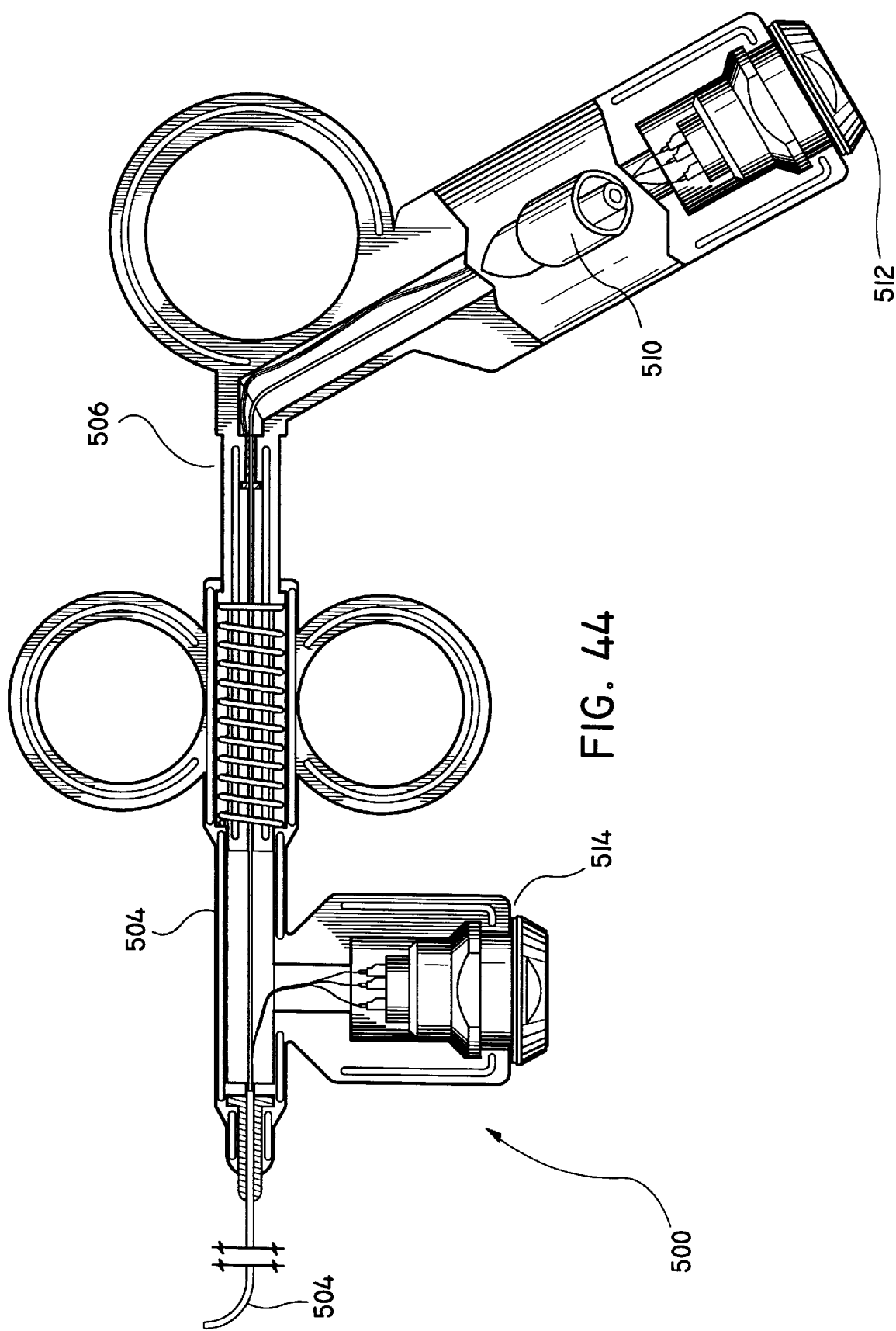
FIG. 44 is a side plan view of the apparatus with the handle in partial cross-section.
Figures 49, 50:
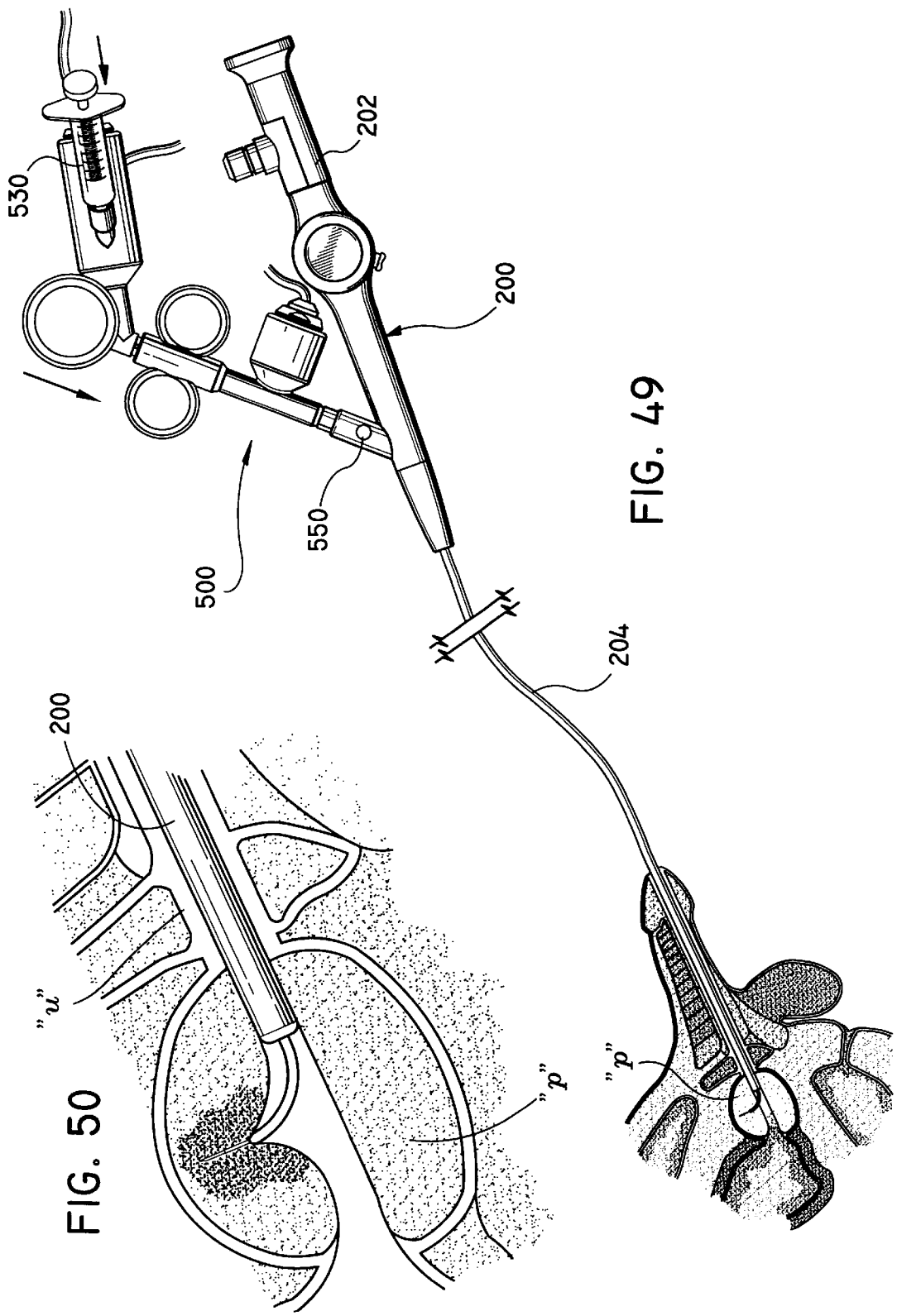
FIG. 49 is a view illustrating the cystoscope and mounted thermal treatment apparatus inserted within the urethral passage.
FIG. 50 is an isolated view illustrating deployment of the electrode assembly within the prostatic tissue.

With reference now to FIGS. 48–50, use of the apparatus 500 will be described. A syringe 530 containing the dissipating fluid, e.g. hypertonic saline solution, is connected to infusion port 510. In the alternative, a fluid bag may also be utilized and connected to the port in a conventional manner. With the cystoscope 200 accessing the urethral passage, the apparatus 500 is inserted and the needle electrode 526 is deployed by advancing actuating portion 506. Prior to and during treatment, i.e. energiziation of the system to apply RF energy saline solution is infused with syringe 530 through the hollow passage of electrode 526 and into the treatment site to facilitate dissipation of the thermal energy and to assist in focusing the current on the target tissue. Preferably, a tube 532 is provided (FIG. 44) to fluidly connect port 510 and the inner passageway of electrode 526. During treatment, the temperature of the treatment area and area adjacent the treatment area may be monitored with thermocouples 516, 522. Other fluids can be injected through the hollow passage of electrode 526 such as an anesthetic agents or drugs post op to minimize edema.

Port 550 can be provided for suction or irrigation, e.g. injection of isotomic saline in the working channel in the space surrounding the delivery tubes.

Figure 51:
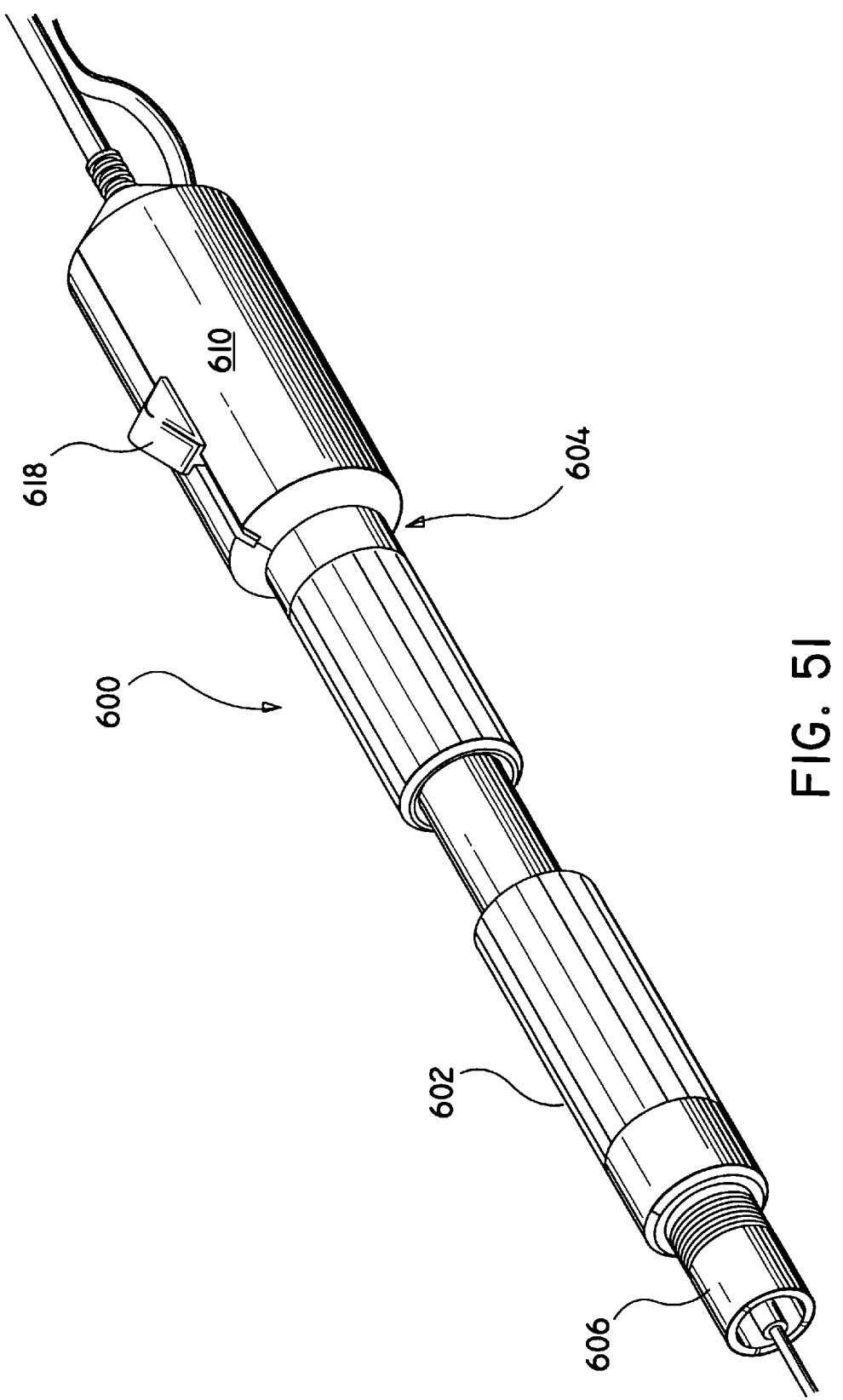
FIG. 51 is a perspective view of an alternate embodiment of a handle to be utilized with the monopolar electrode embodiments of FIGS. 37–48.
Figure 52:
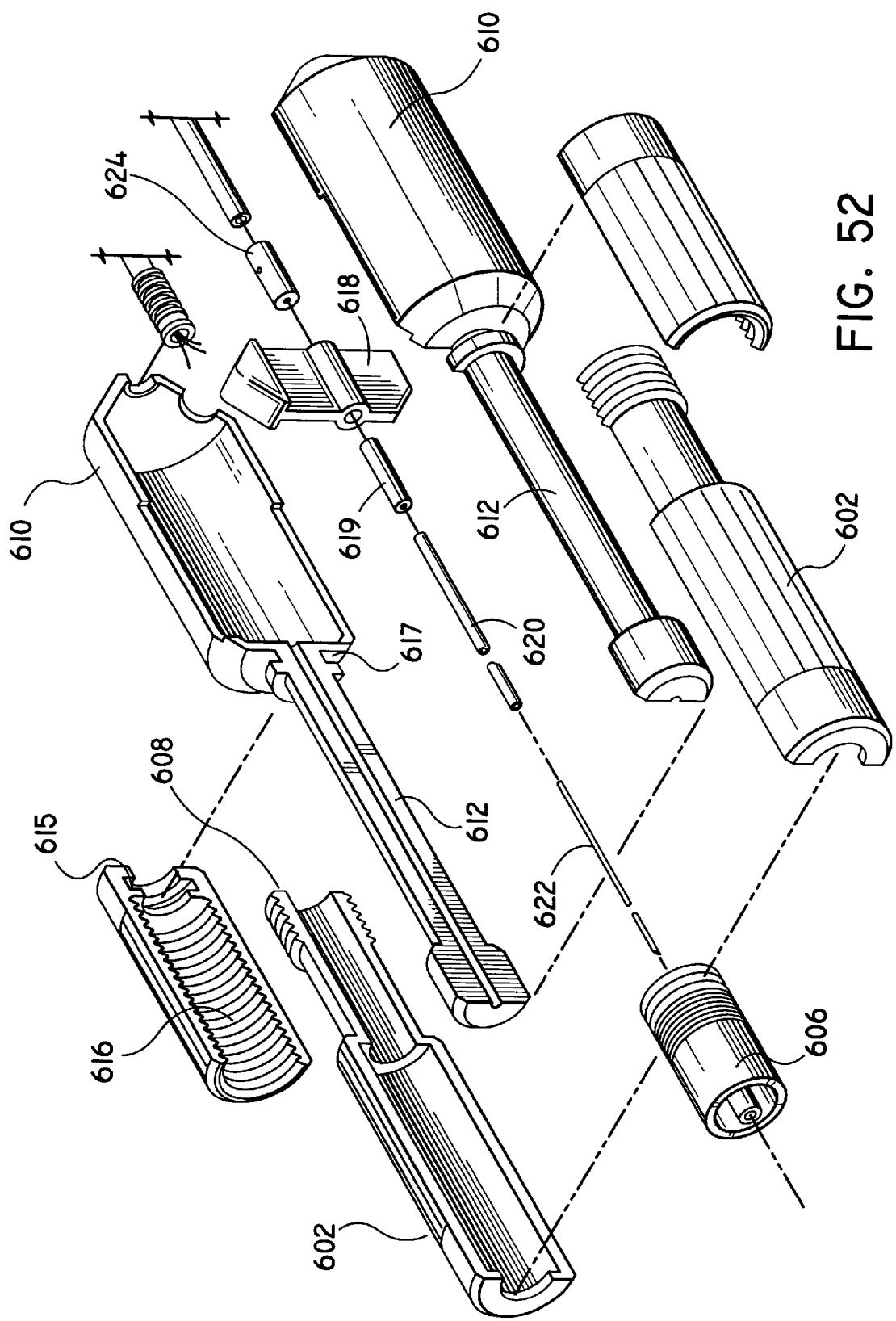
FIG. 52 is a perspective view with parts separated of the handle of FIG. 51.
Figure 53:
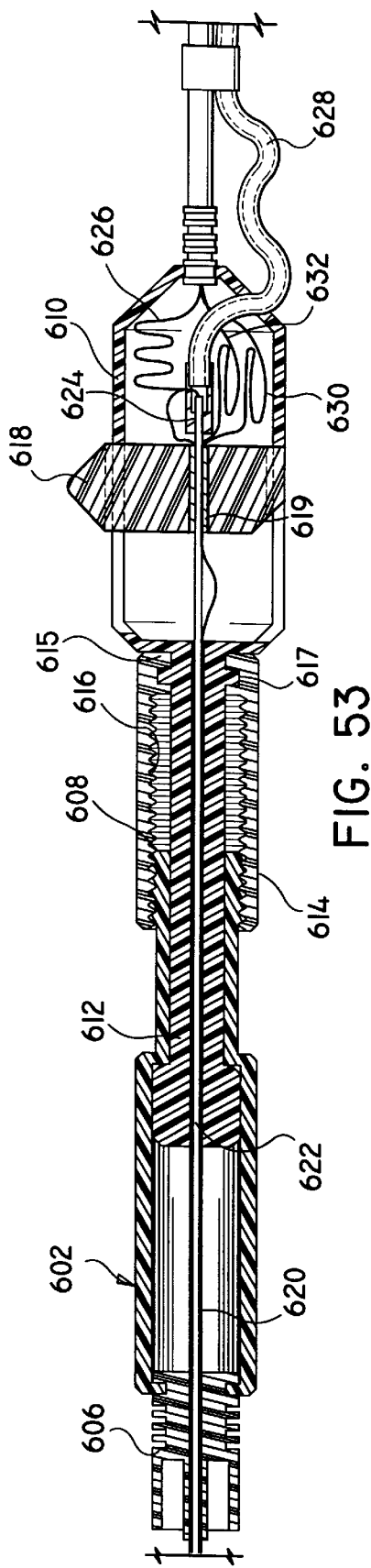
FIG. 53 is a side cross-sectional view of the handle in an unactuated position.

Referring now to FIGS. 51–53, there is illustrated an alternate handle of the apparatus of the present disclosure. Handle 600 is contemplated for use with a monopolar electrode assembly, i.e., those depicted in FIGS. 37–41 and FIGS. 42–48. Elongated handle 600 includes stationary housing portion 602 and movable housing portion 604 which is longitudinal moveable relative to stationary housing portion 602. Stationary housing portion 602 has a mounting collar 606 mounted at its distal end which supports the elongate body of the apparatus. Stationary housing portion 602 further defines at its proximal end a threaded portion 608. Movable portion 604 includes a frame 610 and an elongated drive portion 612 extending from the frame 610. The elongated drive portion 612 is at least partially accommodated within the axial bore of stationary housing 602 and is adapted to move within the stationary housing 602 to deploy the delivery catheter as will be discussed.

A rotatable control member 614 is coaxially mounted about elongated drive portion 612. Rotatable control member 614 is longitudinally fixed with respect to movable housing portion 604 through an interfitting relationship of a locking groove and collar arrangement. More particularly, rotatable control member 614 includes a collar 615 which fits within a groove 617 of movable housing portion 604 to longitudinally fix the rotatable control member 614 to the movable housing portion 604. Rotatable control member 614 has an internal thread 616 which cooperates with threaded portion 608 of stationary housing 602 to longitudinally move the movable housing portion 604 upon rotation of the control member 614.

A deployment member 618 is mounted within the main frame 610 of movable housing 604 and is adapted to move longitudinally with respect to the movable housing portion 604. As will be appreciated from the description provided below, deployment member 618 is connected to the electromagnetic probe and functions in deploying the probe from the distal end of the delivery catheter.

Referring particularly to FIG. 53, in view of FIG. 52, the interrelationship of the delivery catheter and electromagnetic probe with the components of handle 600 will be discussed. The delivery catheter and electromagnetic probe are identical to the delivery catheter and probe discussed in connection with the embodiment of FIG. 37 or in the embodiment of FIG. 42. Delivery catheter 620 extends within handle 600 and through an axial bore of movable housing 604. The proximal end of delivery catheter 620 is longitudinally fixed to elongated portion 612 of movable housing portion 604. Any conventional means for securing delivery catheter 620 to elongated drive portion 612 may be utilized including welding, cements, adhesives, etc.

Accordingly, upon movement of movable housing portion 604 in the longitudinal direction as effectuated through rotation of rotatable control member 614, the delivery catheter 620 also moves longitudinally.

Electromagnetic probe 622 extends through delivery catheter 620 whereby the proximal end of the electromagnetic probe 622 continues within the main frame 610 of the movable housing portion 604. The proximal end of the electromagnetic probe 622 further extends through collar 619 mounted within deployment member 618 and terminates within a ferrule connector 624 disposed proximal of the deployment member 618. Electromagnetic probe 622 is longitudinally secured to collar 619 which is fixed to deployment member 618 such that movement of the deployment member causes corresponding longitudinal motion of the electromagnetic probe. Ferrule connector 624 may be any conventional connector and is preferably mounted within a longitudinal recess or groove defined in the frame of the movable housing portion 604. Ferrule connector 624 is fixed to the proximal end of electromagnetic probe 622 by conventional means including welding, cements, adhesives, etc. and serves to provide the electrical connection between the electromagnetic probe 622 and the service line or cable 626 which supplies the electromagnetic energy from the energy source. Ferrule connector 624 also serves in receiving the saline solution tube 628 to connect the tube to the interior lumen extending within the electromagnetic probe 622.

Also depicted in FIG. 53 are the source lines servicing the two thermocouplers. In particular, the first line 630 services the thermocoupler extending between the outer shrink tubing and delivery catheter (see discussion in connection with embodiment of FIGS. 37–42) which detects or measures the temperature of tissue adjacent the tissue area. The second line 632 services the thermocoupler which extends within the electromagnetic probe 622 for detecting the temperature of the tissue in the treatment area.

Figure 55:
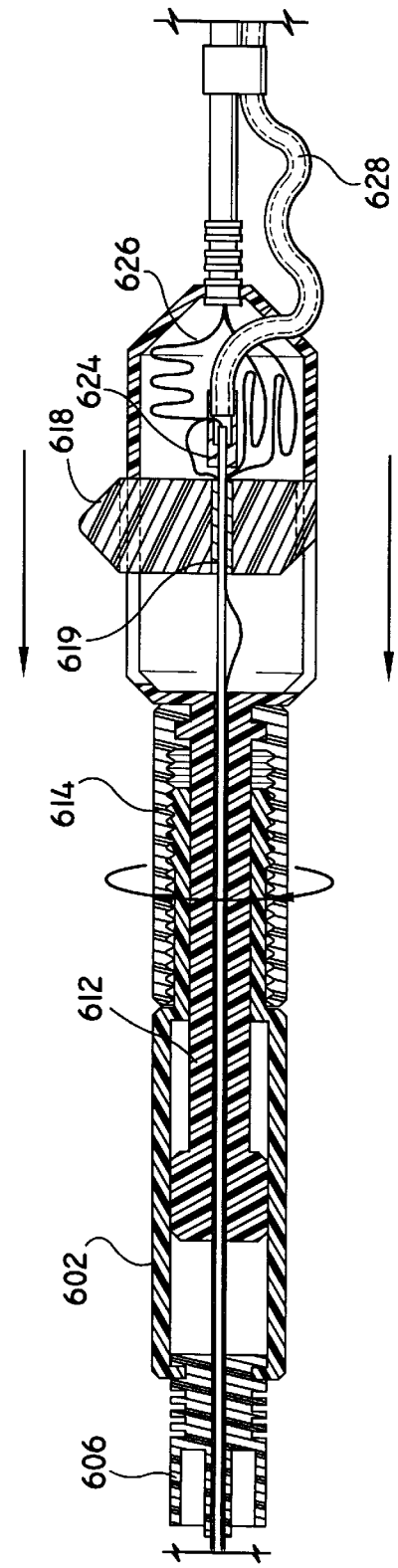
FIG. 55 is a view similar to the view of FIG. 53 illustrating rotation of the control member to selectively deploy the delivery catheter.
Figure 54:
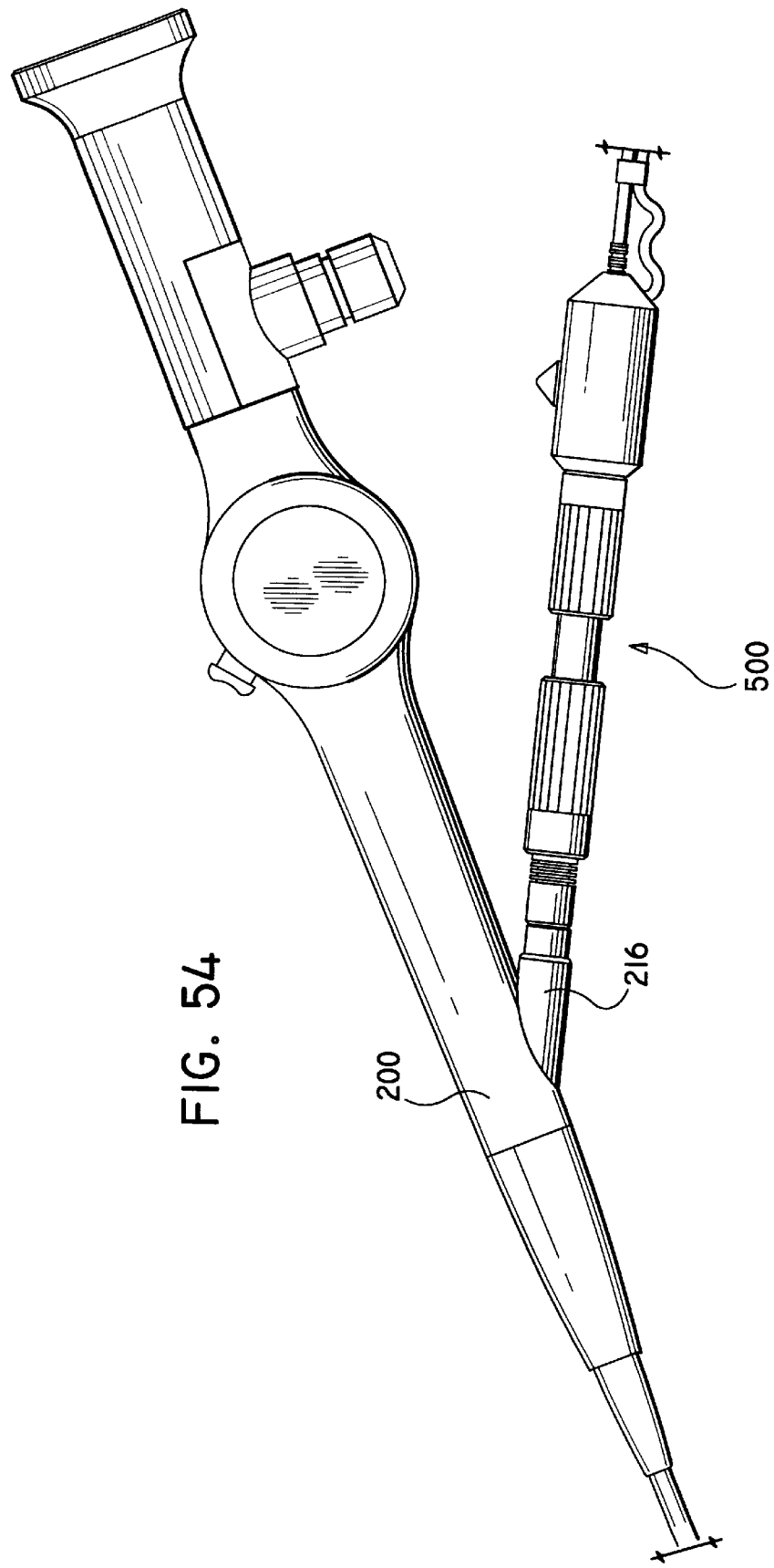
FIG. 54 is a side plan view of the handle of FIG. 51 mounted to a cystoscope.

Referring now to FIG. 54 the use of the apparatus will be discussed. With the cystoscope 200 accessing the urethral passage as discussed above, the elongated portion of the apparatus is inserted within the working channel of the scope and advanced until the handle engages the working channel port connector 216 extending from the proximal end of the working channel of the cystoscope as depicted in FIG. 54. Preferably, handle 600 includes a Luer type connector at its distal end which releasably engages the port connector 216. With reference to FIG. 55, the delivery catheter 620 is deployed by rotating the rotatable control member 614 in the direction depicted in FIG. 55. As rotatable control member 614 rotates, the movable housing portion 604 advances through the threaded engagement of the threaded portions 608, 616 of rotatable control member 614 and the stationary housing 602 thereby advancing the delivery catheter 620 within the elongated portion of the apparatus and beyond the distal end of the working channel of the scope 200. It is appreciated that the rotatable control member 614 can be selectively incrementally rotated to provide selective incremental deployment of the delivery catheter 620, thus, providing enhanced control over the amount of deployment of the memory portion thereof. In effect, therefore, the angular orientation of the distal end of the delivery catheter 620 can be varied through the amount of deployment of the memory portion to achieve desired paths of entry into urethral tissue.

Figure 56:
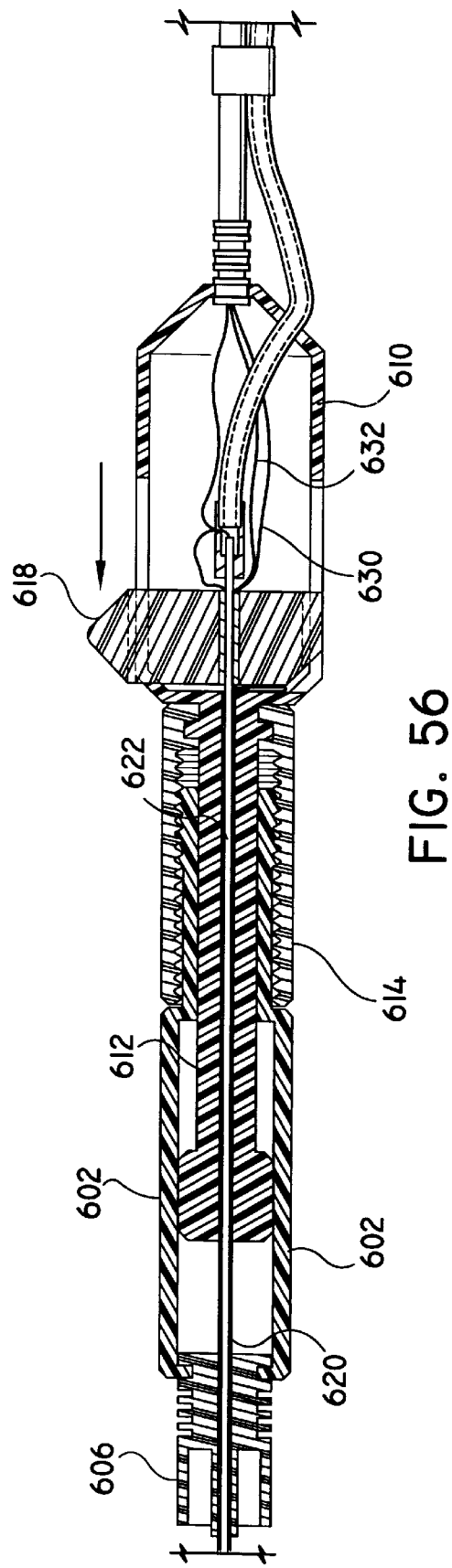
FIG. 56 is a view similar to the view of FIG. 53 illustrating the deployment member advanced to deploy the electromagnetic probe.

Once the delivery catheter 620 is deployed as desired, the electromagnetic probe 622 is deployed. With reference now to FIG. 56, deployment member 618 is advanced in the direction of the directional arrow to deploy the electromagnetic probe 622 from the end of the deployment catheter. As the deployment member 618 moves in longitudinal direction, the ferrule connector 624 is also carried longitudinally due to the fixing of the proximal end of the electromagnetic probe and the ferrule connector 624 as discussed above. It is to be noted that the service lines 630, 632 servicing both the thermocouplers and the electromagnetic probe 622 have sufficient slack to permit advancing movement of the deployment member 618.

It is also envisioned that the auxiliary apparatus described above can be used other than with a scope. For example, the delivery (directing) tubes can be inserted directly into the urethra or other body lumens. The tubes and electrodes can be monitored by ultrasound, MRI, fluoroscopy or other imaging techniques. Ultrasound can also be used in conjunction with the endoscope to image the needles in the edenoma.

While the above description contains many specifics, these specifics should not be construed as limitations on the scope of the disclosure, but merely as exemplifications of preferred embodiments thereof. For example, microwave or other forms of electromagnetic energy can be utilized. Those skilled in the art will envision many other possible variations that are within the scope and spirit of the disclosure as defined by the claims appended hereto.

What is claimed is:

1. An apparatus for thermal treatment of tissue, which comprises:
    a housing portion dimensioned to be grasped with the hand of a user; and
    an elongate portion connected to the housing portion and extending distally therefrom, the elongate portion dimensioned for insertion within a narrow body passage and defining a longitudinal axis, the elongate portion including:
        at least one delivery catheter having proximal and distal end portions, the one delivery catheter movable relative to the housing portion and in a general longitudinal direction between a retracted position and an advanced position; and
        an electromagnetic probe disposed within the one delivery catheter and moveable in a general longitudinal direction within the one delivery catheter to extend a probe end portion thereof beyond the distal end portion of the one delivery catheter and within tissue, the electromagnetic probe being adapted to follow a path defined by the distal end portion of the one delivery catheter, the electromagnetic probe being connected to a thermal energy source; and
    a control member rotatably mounted to the housing portion and operatively connected to the one delivery catheter, the control member rotatably movable to selectively incrementally move the one delivery catheter in the general longitudinal direction between the retracted position and the advanced position.

2. The apparatus according to claim 1 wherein the electromagnetic probe is a monopolar electrode.

3. The apparatus according to claim 1 including a proximally positioned deployment member operatively connected to the electromagnetic probe, the actuating member moveable to deploy the probe end portion of the electromagnetic probe from the one delivery catheter.

4. The apparatus according to claim 1 wherein the elongate portion includes an outer tube, the outer tube accommodating the one delivery catheter and the electromagnetic probe.

5. The apparatus according to claim 1 wherein the control member is operatively connected to the electromagnetic probe such that movement of the control member to move the one delivery catheter between the retracted and advanced positions causes corresponding longitudinal movement of the electromagnetic probe.

6. The apparatus according to claim 1 including a thermocouple mounted to the elongate portion for detecting temperature of tissue within a treatment area generated by the electromagnetic probe.

7. The apparatus according to claim 1 including a thermocouple mounted to the elongate portion for detecting temperature of tissue adjacent a treatment area generated by the electromagnetic probe.

8. The apparatus according to claim 1 wherein the elongate portion is dimensioned for insertion within a working channel of a cystoscope.

9. An apparatus for thermal treatment of tissue, which comprises:
    a housing portion dimensioned to be grasped with the hand of a user;
    an elongate portion connected to the housing portion and extending distally therefrom, the elongate portion dimensioned for insertion within a narrow body passage and defining a longitudinal axis, the elongate portion including:
        at least one delivery catheter having proximal and distal end portions, the one delivery catheter movable relative to the housing portion and in a general longitudinal direction between a retracted position and an advanced position, the one delivery catheter including a memory portion disposed at the distal end portion thereof, the memory portion comprised of shape memory material and having an arcuate configuration when in a normal unstressed condition thereof to define an arcuate path, the memory portion defining a generally blunt distal end surface; and
        an electromagnetic probe disposed within the one delivery catheter and moveable in a general longitudinal direction within the one delivery catheter to extend a probe end portion thereof beyond the distal end portion of the one delivery catheter and within tissue, the electromagnetic probe being adapted to follow the arcuate path defined by the memory portion of the one delivery catheter, the electromagnetic probe being connected to a thermal energy source; and
    a control member rotatably mounted to the housing portion and operatively connected to the one delivery catheter, the control member rotatably movable to selectively incrementally move the one delivery catheter in the general longitudinal direction between the retracted position and the advanced position.

10. A system for thermal treatment of tissue which comprises:
    an endoscope including an elongate body having a working channel; and
    an auxiliary thermal treatment device including:
        a handle portion;
        an elongate portion connected to the handle portion and extending distally therefrom, the elongate portion dimensioned to be positioned within the working channel of the endoscope and defining a longitudinal axis, the elongate portion including:
            at least one delivery catheter having proximal and distal end portions, the distal end portion defining an angularly offset configuration relative to the longitudinal axis; and an electromagnetic probe disposed within the one delivery catheter and moveable in a general longitudinal direction within the one delivery catheter to extend a probe end portion thereof beyond the distal end portion of the one delivery catheter and within tissue, the electromagnetic probe being adapted to follow the angularly offset configuration of the distal end portion of the one delivery catheter, the electromagnetic probe being connected to a thermal energy source; and a control member mounted with respect to the housing portion and operatively connected to the one delivery catheter, the control member rotatably movable to selectively incrementally move the one delivery catheter in a longitudinal direction relative to the housing portion and within the working channel of the endoscope, to thereby selectively incrementally deploy the distal end portion of the one delivery catheter from the working channel such that the distal end portion assumes the angularly offset configuration thereof; and a deployment member mounted to the handle portion and operatively connected to the electromagnetic probe assembly, the deployment member moveable to deploy the probe end portion of the electromagnetic probe assembly.

11. A system for thermal treatment of tissue, which comprises:

an endoscope including an elongate body having a working channel; and an auxiliary thermal treatment device including:
a handle portion;
an elongate portion connected to the handle portion and extending distally therefrom, the elongate portion dimensioned to be positioned within the working channel of the endoscope and defining a longitudinal axis, the elongate portion including:
at least one delivery catheter having proximal and distal end portions, the distal end portion having a memory portion comprised of shape memory material and defining an arcuate configuration angularly offset relative to the longitudinal axis when in a normal unstressed condition thereof;
an electromagnetic probe disposed within the one delivery catheter and moveable in a general longitudinal direction within the one delivery catheter to extend a probe end portion thereof beyond the distal end portion of the one delivery catheter and within tissue, the electromagnetic probe being adapted to follow the arcuate configuration of the memory portion of the one delivery catheter, the electromagnetic probe being connected to a thermal energy source; and a control member mounted with respect to the housing portion and operatively connected to the one delivery catheter, the control member rotatably movable to selectively incrementally move the one delivery catheter in a longitudinal direction relative to the housing portion and within the working channel of the endoscope, to thereby selectively incrementally deploy the distal end portion of the one delivery catheter from the working channel such that the memory portion assumes the normal unstressed curved configuration thereof; and a deployment member mounted to the handle portion and operatively connected to the electromagnetic probe assembly, the deployment member moveable to deploy the probe end portion of the electromagnetic probe assembly.

12. The system according to claim 11 wherein the electromagnetic probe is configured as a monopolar RF electrode.

13. The system according to claim 11 wherein the working channel of the elongate body of the endoscope includes an axial bore extending through a distal end face of the elongate body.

14. The combination of claim 13 wherein the elongate portion of the thermal treatment device includes an axial bore extending through a distal end face of the elongate portion, the one delivery catheter and the electromagnetic probe being deployed through the distal end face of the elongate portion.

15. The system according to claim 13 wherein the electromagnetic probe defines a hollow passageway, the passageway defining a channel for passage of a dissipating agent.

16. The system according to claim 11 wherein the elongate portion is operatively connected to a source of dissipating agent for facilitating dissipation of thermal energy within the tissue and wherein the dissipating agent is conveyed through a channel extending through the elongate portion.

17. The system according to claim 11 wherein the endoscope includes an optical system for viewing an image of an object.

18. The system according to claim 11 wherein the endoscope includes an illumination system for providing illuminating light.

19. An auxiliary electromagnetic thermal treatment apparatus for use with an endoscope to provide the endoscope with electromagnetic thermal treatment capabilities, which comprises:

a handle portion;
an elongate portion connected to the handle portion and extending distally therefrom, the elongate portion dimensioned to be at least partially inserted within a working channel of an endoscope, the elongate portion including:
at least one delivery tube including a memory portion comprised of a shape memory material and defining a normally unstressed curved configuration, the one delivery tube longitudinally moveable relative to the handle portion to extend the memory portion beyond the working channel of the endoscope such that the memory portion assumes the normal unstressed curved configuration thereof; and
an electromagnetic probe disposed within the one delivery tube and longitudinally moveable relative to the one delivery tube to extend a probe end portion thereof beyond the one delivery tube and within tissue, the electromagnetic probe being adapted to follow the curved configuration of the memory portion of the one delivery tube in the normal unstressed condition thereof; and
an actuating member rotatably mounted to the handle portion and operatively connected to the delivery tube, the actuating member moveable to selectively longitudinally move the delivery tube between a first retracted position and a second advanced position.

20. The auxiliary apparatus according to claim 19 including an actuator mounted to the handle portion and operatively connected to the electromagnetic probe, the actuator moveable to extend the probe end portion beyond the one delivery tube.

21. The auxiliary apparatus according to claim 20 wherein the elongate portion includes a flexible outer sleeve, the one delivery tube being at least partially disposed within the outer sleeve.

22. The auxiliary apparatus according to claim 19 wherein the probe is configured as a monopolar electrode.

23. A method for thermally treating tissue, comprising the steps of:

accessing targeted tissue to be thermally treated with an endoscope;

inserting an auxiliary thermal treatment apparatus at least partially into a working channel of the endoscope, the thermal treatment apparatus including an elongate body dimensioned for insertion into the working channel, at least one delivery tube having a memory portion comprised of a shape memory material, an electromagnetic probe disposed within the one delivery tube and a rotatable control member operatively connected to the one delivery tube;

selectively advancing the one delivery tube through the elongate body by rotating the rotatable control member to extend the memory portion of the one delivery tube beyond the elongate body and beyond the working channel of the endoscope, whereby the memory portion assumes a normal curved unstressed orientation;

advancing the electromagnetic probe within the one delivery tube to extend the distal end portion of the electromagnetic probe beyond the one delivery tube and into the targeted tissue, whereby the electromagnetic probe follows the path defined by the one delivery tube in the normal curved orientation thereof; and supplying electromagnetic energy to the electromagnetic probe to thermally treat the tissue.

24. The method of claim 23 wherein the step of advancing the electromagnetic probe includes activating a proximally positioned actuator connected to the electromagnetic probe to selectively advance the electromagnetic probe.

25. The method of claim 24 wherein the step of accessing includes positioning the endoscope within a urethral passage and wherein the step of advancing includes introducing the distal end position of the electromagnetic probe within prostatic tissue.

* * * * *